(12) United States Patent
Estes et al.

(10) Patent No.: US 8,192,395 B2
(45) Date of Patent: Jun. 5, 2012

(54) SYSTEM FOR PROVIDING BLOOD GLUCOSE MEASUREMENTS TO AN INFUSION DEVICE

(75) Inventors: Mark C. Estes, Simi Valley, CA (US); Cary D. Talbot, Santa Clarita, CA (US); "Mike" Charles Vallet Tolle, Van Nuys, CA (US); Jay A. Yonemoto, Arcadia, CA (US)

(73) Assignee: Medtronic MiniMed, inc., Northridge, CA (US)

( * ) Notice: Subject to any disclaimer, the term of this patent is extended or adjusted under 35 U.S.C. 154(b) by 61 days.

(21) Appl. No.: 12/756,544

(22) Filed: Apr. 8, 2010

(65) Prior Publication Data

US 2010/0198143 A1 Aug. 5, 2010

(51) Int. Cl.
A61M 31/00 (2006.01)
A61B 5/00 (2006.01)
(52) U.S. Cl. .......................... 604/66; 600/316; 600/365
(58) Field of Classification Search .............. 604/65–67, 604/890.1, 891.1, 892.1; 600/300, 309, 319, 600/347, 365, 316
See application file for complete search history.

(56) References Cited

U.S. PATENT DOCUMENTS

| | | |
|---|---|---|
| 3,631,847 A | 1/1972 | Hobbs, Ii |
| 4,270,532 A | 6/1981 | Franetzki et al. |
| 4,282,872 A | 8/1981 | Franetzki et al. |
| 4,373,527 A | 2/1983 | Fischell |
| 4,392,849 A | 7/1983 | Petre et al. |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,469,481 A | 9/1984 | Kobayashi |
| 4,475,901 A | 10/1984 | Kraegen et al. |
| 4,494,950 A | 1/1985 | Fischell |
| 4,529,401 A | 7/1985 | Leslie et al. |
| 4,542,532 A | 9/1985 | McQuilkin |
| 4,550,731 A | 11/1985 | Batina et al. |

(Continued)

FOREIGN PATENT DOCUMENTS

DE 4329229 A1 3/1995
(Continued)

OTHER PUBLICATIONS

Bode, BW et al., "Reduction in Severe Hypoglycemia with Long-Term Continuous Subcutaneous Insulin Infusion in Type I Diabetes", Diabetes Care, vol. 19, No. 4, 324-327 (1996).

(Continued)

Primary Examiner — Matthew F Desanto
(74) Attorney, Agent, or Firm — Medtronic MiniMed, Inc.

(57) ABSTRACT

An infusion system includes a characteristic determining device and an infusion device. The characteristic determining device includes a receptacle for receiving and testing an analyte from the user to determine a concentration of the analyte in the user. The characteristic determining device also includes a communication system for transmitting a communication including data indicative of the determined concentration of the analyte in the user, and the infusion device includes a communication system for receiving the communication from the characteristic determining device. The infusion device further includes a bolus estimator for calculating an estimated amount of fluid to be infused into the body of the user based upon the received data indicative of the determined concentration of the analyte in the user and a target concentration of the analyte in the user, and an indicator to indicate when the estimated amount of fluid to be infused has been calculated.

14 Claims, 6 Drawing Sheets

U.S. PATENT DOCUMENTS

| | | |
|---|---|---|
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,696,671 A | 9/1987 | Epstein et al. |
| 4,703,756 A | 11/1987 | Gough et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 4,935,105 A | 6/1990 | Churchouse |
| 4,953,552 A | 9/1990 | DeMarzo |
| 5,019,974 A | 5/1991 | Beckers |
| 5,034,004 A | 7/1991 | Crankshaw |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,113,869 A | 5/1992 | Nappholz et al. |
| 5,153,827 A | 10/1992 | Coutré et al. |
| 5,165,407 A | 11/1992 | Wilson et al. |
| 5,211,626 A | 5/1993 | Frank et al. |
| 5,216,597 A | 6/1993 | Beckers |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,266,013 A | 11/1993 | Aubert et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutré et al. |
| 5,319,363 A | 6/1994 | Welch et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,364,346 A | 11/1994 | Schrezenmeir |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,417,222 A | 5/1995 | Dempsey et al. |
| 5,429,602 A | 7/1995 | Hauser |
| 5,437,634 A | 8/1995 | Amano |
| 5,464,392 A | 11/1995 | Epstein et al. |
| 5,472,317 A | 12/1995 | Field et al. |
| 5,478,211 A | 12/1995 | Dominiak et al. |
| 5,482,446 A | 1/1996 | Williamson et al. |
| 5,482,473 A | 1/1996 | Lord et al. |
| 5,485,408 A | 1/1996 | Blomquist |
| 5,497,772 A | 3/1996 | Schulman et al. |
| 5,499,243 A | 3/1996 | Hall |
| 5,507,288 A | 4/1996 | Böcker et al. |
| 5,543,326 A | 8/1996 | Heller et al. |
| 5,545,191 A | 8/1996 | Mann et al. |
| 5,558,640 A | 9/1996 | Pfeiler et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,584,814 A | 12/1996 | Schuster et al. |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,609,575 A | 3/1997 | Larson et al. |
| 5,616,124 A | 4/1997 | Hague et al. |
| 5,620,312 A | 4/1997 | Hyman et al. |
| 5,626,144 A | 5/1997 | Tacklind et al. |
| 5,630,710 A | 5/1997 | Tune et al. |
| 5,643,212 A | 7/1997 | Coutré et al. |
| 5,647,853 A | 7/1997 | Feldmann et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,681,285 A | 10/1997 | Ford et al. |
| 5,685,844 A | 11/1997 | Marttila |
| 5,687,734 A | 11/1997 | Dempsey et al. |
| 5,704,366 A | 1/1998 | Tacklind et al. |
| 5,713,856 A | 2/1998 | Eggers et al. |
| 5,748,103 A | 5/1998 | Flach et al. |
| 5,750,926 A | 5/1998 | Schulman et al. |
| 5,764,159 A | 6/1998 | Neftel |
| 5,772,635 A | 6/1998 | Dastur et al. |
| 5,777,060 A | 7/1998 | Van Antwerp |
| 5,779,665 A | 7/1998 | Mastrototaro et al. |
| 5,786,439 A | 7/1998 | Van Antwerp et al. |
| 5,788,669 A | 8/1998 | Peterson |
| 5,791,344 A | 8/1998 | Schulman et al. |
| 5,807,336 A | 9/1998 | Russo et al. |
| 5,814,015 A | 9/1998 | Gargano et al. |
| 5,832,448 A | 11/1998 | Brown |
| 5,840,020 A | 11/1998 | Heinonen et al. |
| 5,840,026 A | 11/1998 | Uber, III et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,951,521 A | 9/1999 | Mastrototaro et al. |
| 5,956,501 A | 9/1999 | Brown |
| 5,960,403 A | 9/1999 | Brown |
| 5,961,451 A | 10/1999 | Reber et al. |
| 5,965,380 A | 10/1999 | Heller et al. |
| 5,972,199 A | 10/1999 | Heller et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,067,474 A | 5/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,135,949 A | 10/2000 | Russo et al. |
| 6,142,008 A | 11/2000 | Cole et al. |
| 6,143,164 A | 11/2000 | Heller et al. |
| 6,162,611 A | 12/2000 | Heller et al. |
| 6,171,276 B1 | 1/2001 | Lippe et al. |
| 6,175,752 B1 | 1/2001 | Say et al. |
| 6,246,992 B1 | 6/2001 | Brown |

| | | | |
|---|---|---|---|
| 6,248,067 B1 | 6/2001 | Causey, III et al. | |
| 6,250,309 B1 | 6/2001 | Krichen et al. | |
| 6,254,586 B1 | 7/2001 | Mann et al. | |
| 6,259,937 B1 | 7/2001 | Schulman et al. | |
| 6,269,340 B1 | 7/2001 | Ford et al. | |
| 6,270,478 B1 | 8/2001 | Mernoe | |
| 6,270,481 B1 | 8/2001 | Mason et al. | |
| 6,295,506 B1 | 9/2001 | Heinonen et al. | |
| 6,329,161 B1 | 12/2001 | Heller et al. | |
| 6,355,018 B1 | 3/2002 | Vasko | |
| 6,461,331 B1 | 10/2002 | Van Antwerp | |
| 6,472,122 B1 | 10/2002 | Schulman et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,551,276 B1 | 4/2003 | Mann et al. | |
| 6,554,798 B1 | 4/2003 | Mann et al. | |
| 6,556,963 B1 | 4/2003 | Tetzlaff | |
| 6,558,320 B1 | 5/2003 | Causey, III et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,671,554 B2 | 12/2003 | Gibson et al. | |
| 6,676,816 B2 | 1/2004 | Mao et al. | |
| 6,689,091 B2 | 2/2004 | Bui et al. | |
| 6,689,265 B2 | 2/2004 | Heller et al. | |
| 6,733,471 B1 | 5/2004 | Ericson et al. | |
| 6,746,582 B2 | 6/2004 | Heller et al. | |
| 6,749,740 B2 | 6/2004 | Liamos et al. | |
| 6,809,653 B1 | 10/2004 | Mann et al. | |
| 6,872,200 B2 | 3/2005 | Mann et al. | |
| 6,881,551 B2 | 4/2005 | Heller et al. | |
| 6,893,545 B2 | 5/2005 | Gotoh et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,936,029 B2 | 8/2005 | Mann et al. | |
| 6,942,518 B2 | 9/2005 | Liamos et al. | |
| 6,945,760 B2 | 9/2005 | Gray et al. | |
| 6,979,326 B2 | 12/2005 | Mann et al. | |
| 6,997,920 B2 | 2/2006 | Mann et al. | |
| 7,025,732 B2 | 4/2006 | Thompson et al. | |
| 7,278,983 B2 * | 10/2007 | Ireland et al. | 604/66 |
| 2002/0082665 A1 | 6/2002 | Haller et al. | |
| 2002/0161288 A1 | 10/2002 | Shin et al. | |
| 2003/0078560 A1 | 4/2003 | Miller et al. | |
| 2003/0088166 A1 | 5/2003 | Say et al. | |
| 2003/0152823 A1 | 8/2003 | Heller | |
| 2003/0168338 A1 | 9/2003 | Gao et al. | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0212379 A1 * | 11/2003 | Bylund et al. | 604/504 |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0074785 A1 | 4/2004 | Holker et al. | |
| 2004/0093167 A1 | 5/2004 | Braig et al. | |
| 2004/0111017 A1 | 6/2004 | Say et al. | |
| 2005/0214585 A1 | 9/2005 | Li et al. | |

FOREIGN PATENT DOCUMENTS

| | | |
|---|---|---|
| EP | 0098592 A2 | 1/1984 |
| EP | 0680727 A1 | 11/1995 |
| EP | 0806738 A1 | 11/1997 |
| EP | 0880936 A2 | 12/1998 |
| EP | 1048264 A1 | 11/2000 |
| EP | 1338295 A1 | 8/2003 |
| GB | 2218831 A | 11/1989 |
| WO | 9528878 A1 | 11/1995 |
| WO | 9620745 A1 | 7/1996 |
| WO | 9636389 A1 | 11/1996 |
| WO | 9637246 A1 | 11/1996 |
| WO | 9721456 A1 | 6/1997 |
| WO | 9728736 A1 | 8/1997 |
| WO | 9800056 A1 | 1/1998 |
| WO | 9820439 A1 | 5/1998 |
| WO | 9824358 A2 | 6/1998 |
| WO | 9842407 A1 | 10/1998 |
| WO | 9849659 A2 | 11/1998 |
| WO | 9856293 A1 | 12/1998 |
| WO | 9859487 A1 | 12/1998 |
| WO | 9908183 A1 | 2/1999 |
| WO | 9910801 A1 | 3/1999 |
| WO | 9918532 A1 | 4/1999 |
| WO | 9922236 A1 | 5/1999 |
| WO | 9945375 A1 | 9/1999 |
| WO | 9945387 A2 | 9/1999 |
| WO | 9956613 A1 | 11/1999 |
| WO | 0019887 A1 | 4/2000 |
| WO | 0047109 A1 | 8/2000 |
| WO | 0078210 A1 | 12/2000 |
| WO | 0128416 A1 | 4/2001 |
| WO | 0128495 A2 | 4/2001 |
| WO | 0139089 A1 | 5/2001 |
| WO | 0152718 A2 | 7/2001 |
| WO | 0152727 A1 | 7/2001 |
| WO | 0156454 A2 | 8/2001 |
| WO | 02058537 A2 | 8/2002 |

OTHER PUBLICATIONS

Boland, E, Teens Pumping it Up! Insulin Pump Therapy Guide for Adolescents, 2nd Edition (1998).

Brackenridge, BP, "Carbohydrate Gram Counting: A Key to Accurate Mealtime Boluses in Intensive Diabetes Therapy", Practical Diabetology, vol. 11, No. 2, pp. 22-28 (1992).

Brackenridge, BP et al., Counting Carbohydrates: How to Zero in on Good Control using the MiniMed insulin pump, MiniMed Technologies Inc. (1995).

Farkas-Hirsch, R et al. "Continuous Subcutaneous Insulin Infusion: A Review of the Past and Its Implementation for the Future", Diabetes Spectrum From Research to Practice, vol. 7, No. 2, pp. 80-84, 136-138 (1994).

Hirsch, IB et al., "Intensive Insulin Therapy for Treatment of Type I Diabetes", Diabetes Care, vol. 13, No. 12, pp. 1265-1283 (1990).

Kulkarni, K et al., "Carbohydrate Counting: A Primer for Insulin Pump Users to Zero in on Good Control", MiniMed Inc. (1999).

Marcus, AO et al., "Insulin Pump Therapy: Acceptable Alternative to Injection Therapy", Postgraduate Medicine, vol. 99, No. 3, pp. 125-143 (1996).

Reed, J, "Living with Diabetes", Voice of the Diabetic, vol. 11, No. 3, pp. 1-38 (1996).

Skyler, JS, "Continuous Subcutaneous Insulin Infusion [CSII] With External Devices: Current Status", Update in Drug Delivery Systems, Futura Publishing Company, Chapter 13, pp. 163-183 (1989).

Skyler, JS et al., The Insulin Pump Therapy Book: Insights from the Experts, MiniMed Technologies (1995).

Strowig, SM, "Initiation and Management of Insulin Pump Therapy", The Diabetes Educator, vol. 19, No. 1, pp. 50-60 (1993).

Walsh, J et al., Pumping Insulin: The Art of Using an Insulin Pump, Published by MiniMed Technologies (1989).

"Insulin Infusion Pump Therapy," pp. 66-78, Intensive Diabetes Management, 1995.

MiniMed Dosage Calculator Initial Meal Bolus Guidelines/ MiniMed Dosage Calculator Intial Basal Rate Guidelines Percentage Method, MiniMed, 4 pages, 1994.

MiniMed 508 Flipchart: Guide to Insulin Pump Therapy (1999).

MiniMed Now I Can Correction Bolus Calculator/MiniMed Now I Can Meal Bolus Calculator (Jul. 2000).

MiniMed Now I Can brochure (Sep. 2000).

MiniMed Now I Can MiniMed Diabetes Management packet (Sep. 2000).

Medtronic MiniMed Meal Bolus Calculator and Correction Bolus Calculator; International Version (Feb. 2002).

User's Guide for 508 Insulin Pump, Medtronic MiniMed (Sep. 2001).

Medtronic MiniMed Paradigm Infusion Pump Model MMT-511 User Guide (Jan. 2002).

Abel, P. et al., "Experience with an implantable glucose sensor as a prerequisite of an artificial beta cell", Biomed. Biochim. Acta 43 (1984) 5, pp. 577-584.

Kawamori, R. et al., "Perfect Normalization of Excessive Glucagon Responses to Intravenous Arginine in Human Diabetes Mellitus with the Artificial Beta-Cell", Rapid Publication from Diabetes, vol. 29, (Sep. 1980), pp. 762-765.

Mastrototaro, John J. et al., "An Electroenzymatic Sensor Capable of 72 Hour Continuous Monitoring of Subcutaneous Glucose", Presentation given at the 14th International Diabetes Federation Congress in Washington, D.C., (Jun. 23-28, 1991), 19 pages.

McKean, B., et al., "A Telemetry-Instrumentation System for Chronically Implanted Glucose and Oxygen Sensors", IEEE Transactions on Biomedical Engineering, (Jul. 1988), vol. 35, No. 7, pp. 526-532.

Monroe, D., "Novel implantable glucose sensors", ACL, (Dec. 1989), pp. 8-16.

Nishida, K. et al., "Clinical applications of the wearable artificial endocrine pancreas with the newly designed needle-type glucose sensor", (Elsevier Science B.V.), (1994), pp. 353-358.

Shichiri, M. et al., "An artificial endocrine pancreas—problems awaiting solution for long-term clinical applications of a glucose sensor", Frontiers Med. Biol. Engng, (VSP), (1991), vol. 3., No. 4, pp. 283-292.

Shichiri, M. et al., "Wearable Artificial Endocrine Pancreas with Needle-Type Glucose Sensor", The Lancet, (Nov. 20, 1982), pp. 1129-1131.

Shichiri, M. et al., "Telemetry Glucose Monitoring Device with Needle-Type Glucose Sensor: A Useful Tool for Blood Glucose Monitoring in Diabetic Individuals", Diabetes Care, (May-Jun. 1986), vol. 9, No. 3, pp. 298-301.

Shichiri, M. et al., "Normalization of the Paradoxic Secretion of Glucagon in Diabetics Who Were Controlled by the Artifical Beta Cell", Diabetes, (Apr. 1979), vol. 28, pp. 272-275.

Shichiri, M. et al., "Closed-Loop Glycemic Control with a Wearable Artificial Endocrine Pancreas Variations in Daily Insulin Requirements to Glycemic Response", Rapid Publication from Diabetes, vol. 33, (Dec. 1984), pp. 1200-1202.

Shichiri, M. et al., "A Needle-Type Glucose Sensor—A Valuable Tool Not Only for a Self-Blood Glucose Monitoring But for a Wearable Artificial Pancreas-", Life Support Systems, Proceedings XI Annual Meeting ESAO Alpbash-Innsbruck Austria, (Sep. 1984), vol. 2, Supplement 1, pp. 7-9.

Shichiri, M. et al., "The Wearable Artificial Endocrine Pancreas with a Needle-Type Glkucose Sensor: Perfect Glycemic Control in Ambulatory Diabetics", Acta Paediatr Jpn 26, (1984), pp. 359-370.

Shichiri, M. et al., "Glycaemic Control in Pancreatectomized Dogs with a Wearable Artificial Endocrine Pancreas", Diabetologia 24, (1983), pp. 179-184.

Shults, M.C. et al., "A Telemetry-Instrumentation System for Monitoring Multiple Subcutaneously Implanted Glucose Sensors", IEEE Transactions on Biomedical Engineering, (1994), vol. 41, No. 10, pp. 937-942.

Wang, J. et al., "Needle-Type Dual Microsensor for the Simultaneous Monitoring of Glucose and Insulin", Analytical Chemistry, (Feb. 15, 2001), vol. 73, No. 4, pp. 844-847.

Furler, SM et al., "Development and testing of a simple algorithm for a glucose clamp," Medical & Biological Engineering & Computing (Jul. 1986 UK) (vol. 24, No. 4, pp. 365-370, XP0022589180, ISSN: 0140-0118, p. 367, left hand column, lines 23-29).

International Search Report for International Application No. PCT/US03/22862 filed Jul. 23, 2003.

\* cited by examiner

SYSTEM FOR PROVIDING BLOOD GLUCOSE MEASUREMENTS TO AN INFUSION DEVICE

RELATED APPLICATIONS

This application is a continuation application of U.S. patent application Ser. No. 10/624,389 filed Jul. 22, 2003 now abandoned, which claims priority from U.S. Provisional Applications No. 60/398,199 filed Jul. 24, 2002 and No. 60/412,998 filed Sep. 23, 2002, all of which are herein incorporated by reference.

FIELD OF THE INVENTION

This invention relates generally to infusion systems that are used for infusing a fluid into a user, and in particular, to apparatuses and methods for providing blood glucose measurements to an infusion device.

BACKGROUND OF THE INVENTION

Patients with Type 1 diabetes and some patients with Type 2 diabetes use insulin to control their blood glucose (BG) level. Typically, if a patient's BG level is too high, the patient can inject a "bolus" (dose) of insulin to lower his/her BG level from its present level to a desired target level. Furthermore, patients may inject a bolus of insulin in anticipation of ingesting carbohydrates, thus heading off a sharp rise in their BG level. Patients employ various calculations to determine the amount of insulin to inject. Bolus estimation software is available for calculating an insulin bolus. Patients may use these software programs on an electronic computing device, such as a computer, the Internet, a personal digital assistant (PDA), or an insulin delivery device. Insulin delivery devices include infusion pumps, injection pens, and IV meters. The best bolus estimation software takes into account the patient's present BG level. Presently, a patient must measure his/her blood glucose using a BG measurement device, such as a test strip meter, a continuous glucose measurement system, or a hospital hemacue. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. Then the patient may visually read the BG measurement and physically enter the BG measurement into an electronic computing device to calculate a bolus estimate. Finally, once the bolus estimate is calculated, the patient must inject the insulin bolus or program an insulin delivery device to deliver the bolus into their body. Unfortunately, this process is cumbersome and is subject to transcribing errors—for example, the patient may inaccurately enter the BG measurement that is displayed on the BG measurement device into the electronic computing device. Thus, if the BG measurement is not entered correctly, the bolus estimate is not accurate, which may lead to the delivery of an inappropriate insulin dose.

SUMMARY OF THE INVENTION

In preferred embodiments of the present invention, an infusion system for infusing a fluid into a body of a user includes a characteristic determining device and an infusion device. The characteristic determining device includes a housing adapted to be carried by the user, a receptacle coupled to the housing for receiving and testing an analyte from the user to determine a concentration of the analyte in the user, a processor contained in the housing and coupled to the receptacle for processing the determined concentration of the analyte from the receptacle, and a communication system contained in the housing and coupled to the processor for transmitting a communication including data indicative of the determined concentration of the analyte in the user. In particular embodiments, the characteristic determining device may also include a lancing device coupled to the receptacle for obtaining the analyte from the user. In preferred embodiments, the infusion device includes a housing adapted to be carried by the user, a drive mechanism contained in the housing and operatively coupled with a reservoir containing the fluid for infusing the fluid into the body of the user, a communication system contained in the housing for receiving the communication including the data indicative of the determined concentration of the analyte in the user from the determining device, and a processor contained in the housing and coupled to the communication system for processing the data indicative of the determined concentration of the analyte in the user and controlling the infusion device. The infusion device further includes a bolus estimator used in conjunction with the processor for calculating an estimated amount of fluid to be infused into the body of the user based upon the received data indicative of the determined concentration of the analyte in the user and a target concentration of the analyte in the user, and an indicator to indicate when the estimated amount of fluid to be infused has been calculated. Additionally, the infusion device may include a user input device for inputting an estimate of a material to be ingested by the user, and the bolus estimator may include the capability to calculate the estimated amount of fluid to be infused into the body of the user based upon the inputted estimate of the material to be ingested by the user. The infusion device may also include a memory for storing the data indicative of the determined concentration of the analyte in the user received by the infusion device communication system from the determining device communication system.

In particular embodiments, the characteristic determining device automatically transmits the communication including the data indicative of the determined concentration of the analyte in the user to the infusion device. In other particular embodiments, the characteristic determining device further includes a user input device for inputting commands, and transmits the communication including the data indicative of the determined concentration of the analyte in the user to the infusion device in response to a command from the user input device. In additional embodiments, the characteristic determining device further includes an indicator to indicate a status of the communication including the data indicative of the determined concentration of the analyte in the user being transmitted from the determining device communication system to the infusion device communication system.

In some embodiments, the communication transmitted from the characteristic determining device to the infusion device further includes a time at which the concentration of the analyte in the user was determined. In additional embodiments, the processor of the characteristic determining device determines an amount of time that has elapsed since the concentration of the analyte in the user was determined, and the communication transmitted from the determining device to the infusion device further includes the elapsed amount of time. Further, the processor of the characteristic determining device may cause the communication system of the characteristic determining device not to transmit the communication including the data indicative of the determined concentration of the analyte in the user if the elapsed amount of time exceeds a predetermined amount of time. In other embodiments, the infusion device processor determines an amount of time that has elapsed since the data indicative of the determined concentration of the analyte in the user was received, and causes the bolus estimator not to calculate the estimated amount of fluid to be infused based upon the determined concentration of the analyte if the elapsed amount of time exceeds a predetermined amount of time. In still other embodiments, the processor of the infusion device determines an amount of time that has elapsed since the concentration of the analyte in the user was determined, and causes the bolus estimator not to calculate the estimated amount of fluid to be infused based upon the determined concentration of the analyte if the elapsed amount of time exceeds a predetermined amount of time.

In further embodiments, the determining device communication system is capable of being deactivated and reactivated. The characteristic determining device includes a user input device for inputting commands, and the communication system of the characteristic determining device is capable of being deactivated in response to a first command from the user input device and being reactivated in response to a second command from the user input device. Alternatively, the communication system of the characteristic determining device may be automatically reactivated after a predetermined amount of time has elapsed or at a predetermined time of day. Additionally, the characteristic determining device may include a memory for storing data indicative of the determined concentration of the analyte in the user that is determined when the determining device communication system is deactivated, and the determining device communication system may transmit a communication including the stored data to the infusion device communication system when the determining device communication system is reactivated.

In still other embodiments, the processor of the characteristic determining device has unique identification information, and the communication transmitted from the characteristic determining device to the infusion device further includes the unique identification information of the determining device processor such that the infusion device is capable of discerning whether the communication is intended for receipt by the infusion device. In yet other embodiments, the processor of the infusion device has unique identification information, and the communication transmitted from the characteristic determining device to the infusion device further includes the unique identification information of the infusion device processor such that the infusion device is capable of discerning whether the communication is intended for receipt by the infusion device.

In preferred embodiments, the processor of the infusion device uses power cycling whereby power is periodically supplied to the communication system of the infusion device until a communication is received from the characteristic determining device. When a communication is received from the characteristic determining device, the processor of the infusion device discontinues using power cycling whereby the power is continuously supplied to the infusion device communication system. The infusion device processor may then resume using power cycling upon completing the receipt of the communication including the data indicative of the determined concentration of the analyte in the user from the determining device communication system.

In particular embodiments, the infusion system further includes a connector for coupling the characteristic determining device to a computer and downloading data from the characteristic determining device to the computer. The communication system of the infusion device is further capable of transmitting a communication including infusion device data to be downloaded, and the communication system of the characteristic determining device is further capable of receiving the communication including the infusion device data to be downloaded from the infusion device. The received infusion device data is then downloaded from the characteristic determining device through the connector to the computer. Alternatively, the characteristic determining device may further include a memory for storing data, and the received infusion device data may be stored in the memory of the characteristic determining device for subsequent downloading through the connector to the computer.

In other particular embodiments, the characteristic determining device further includes a user input device for inputting remote control commands for controlling the infusion device. The communication system of the characteristic determining device further transmits a communication including the remote control commands, and the communication system of the infusion device further receives the communication including the remote control commands from the characteristic determining device. The processor of the infusion device then controls the infusion device in accordance with the received remote control commands.

In yet other particular embodiments, the infusion device further includes a user input device for inputting remote control commands for controlling the characteristic determining device. The communication system of the infusion device further transmits a communication including the remote control commands, and the communication system of the characteristic determining device further receives the communication including the remote control commands from the infusion device. The processor of the characteristic determining device then controls the characteristic determining device in accordance with the received remote control commands.

In additional embodiments, the characteristic determining device further includes a determining device clock, and the infusion device further includes an infusion device clock. The infusion device communication system further transmits a communication including a time of the infusion device clock, and the determining device communication system further receives the communication including the time of the infusion device clock from the infusion device communication system. The determining device clock is then set to the received time of the infusion device clock. Alternatively, the determining device communication system further transmits a communication including a time of the determining device clock, and the infusion device communication system further receives the communication including the time of the determining device clock from the determining device communication system. The infusion device clock is then set to the received time of the determining device clock.

In accordance with another embodiment of the present invention, an infusion device infuses a fluid into a body of a user and is capable of communicating with a characteristic determining device, which is adapted for determining a concentration of an analyte in the user. The infusion device includes a housing adapted to be carried by the user, a drive mechanism contained in the housing and operatively coupled with a reservoir containing the fluid for infusing the fluid into the body of the user, a communication system contained in the housing for receiving a communication including data indicative of the determined concentration of the analyte in the user from the characteristic determining device, and a processor contained in the housing and coupled to the communication system for processing the data indicative of the determined concentration of the analyte in the user and controlling the infusion device. The infusion device also includes a bolus estimator used in conjunction with the processor for calculating an estimated amount of fluid to be infused into the body of the user based upon the received data indicative of the determined concentration of the analyte in the user and a target concentration of the analyte in the user. The infusion device further includes an indicator to indicate when the estimated amount of fluid to be infused has been calculated.

In accordance with still another embodiment of the present invention, a characteristic determining device determines a concentration of an analyte in a body of a user and is capable of communicating with an infusion device, which is adapted for infusing a fluid into the body of the user and calculating an estimated amount of the fluid to be infused into the body of the user based upon the determined concentration of the analyte in the user and a target concentration of the analyte in the user. The characteristic determining device includes a housing adapted to be carried by the user, a receptacle coupled to the housing for receiving and testing an analyte from the user to determine the concentration of the analyte in the user, a processor contained in the housing and coupled to the receptacle for processing the determined concentration of the analyte from the receptacle, and a communication system contained in the housing and coupled to the processor for transmitting a communication including data indicative of the determined concentration of the analyte in the user to the infusion device.

According to yet another embodiment of the present invention, an infusion system includes a characteristic determining device and an infusion device, and a method for infusing a fluid into a body of a user is provided. The method includes the steps of: receiving and testing an analyte from the user to determine a concentration of the analyte in the user, transmitting with the characteristic determining device a communication including data indicative of the determined concentration of the analyte in the user, and receiving with the infusion device the communication including the data indicative of the determined concentration of the analyte in the user. The data indicative of the determined concentration of the analyte in the user received by the infusion device from the characteristic determining device may then be stored in a memory of the infusion device. The method further includes the steps of calculating an estimated amount of fluid to be infused into the body of the user based upon the received data indicative of the determined concentration of the analyte in the user and a target concentration of the analyte in the user, and indicating when the estimated amount of fluid to be infused has been calculated. Additionally, the method may include the step of inputting an estimate of a material to be ingested by the user, and the estimated amount of fluid to be infused into the body of the user is calculated further based upon the inputted estimate of the material to be ingested by the user.

In some embodiments, the communication including the data indicative of the determined concentration of the analyte in the user is automatically transmitted from the characteristic determining device to the infusion device. In other embodiments, the communication including the data indicative of the determined concentration of the analyte in the user is transmitted from the characteristic determining device to the infusion device in response to an inputted command. In still other embodiments, the system indicates a status of the communication including the data indicative of the determined concentration of the analyte in the user being transmitted from the characteristic determining device to the infusion device.

In particular embodiments, the communication including the data indicative of the determined concentration of the analyte in the user transmitted from the characteristic determining device to the infusion device further includes a time at which the concentration of the analyte in the user was determined. In other particular embodiments, the system also determines an amount of time that has elapsed since the concentration of the analyte in the user was determined. In yet other particular embodiments, the system determines an amount of time that has elapsed since the communication including the data indicative of the determined concentration of the analyte in the user was received by the infusion device.

In additional embodiments, the method further includes the steps of transmitting with the infusion device a communication including a clock time of the infusion device, receiving with the characteristic determining device the communication including the clock time of the infusion device, and setting a clock time of the characteristic determining device to the received clock time of the infusion device. Alternatively, the method may include the steps of transmitting with the characteristic determining device a communication including a clock time of the characteristic determining device, receiving with the infusion device the communication including the clock time of the characteristic determining device, and setting a clock time of the infusion device to the received clock time of the characteristic determining device.

In accordance with a further embodiment of the present invention, an infusion system for infusing a fluid into a body of a user includes a characteristic determining device and an infusion device. The characteristic determining device includes a determining device housing adapted to be carried by the user, a sensor coupled to the determining device housing for determining a concentration of an analyte in the user, a determining device processor contained in the determining device housing and coupled to the sensor for processing the determined concentration of the analyte from the sensor, and a determining device communication system contained in the determining device housing and coupled to the determining device processor for transmitting a communication including data indicative of the determined concentration of the analyte in the user. The infusion device includes an infusion device housing adapted to be carried by the user, a drive mechanism contained in the infusion device housing and operatively coupled with a reservoir containing the fluid for infusing the fluid into the body of the user, an infusion device communication system contained in the infusion device housing for receiving the communication including the data indicative of the determined concentration of the analyte in the user from the determining device communication system, and an infusion device processor contained in the infusion device housing and coupled to the infusion device communication system for processing the data indicative of the determined concentration of the analyte in the user and controlling the infusion device.

In particular embodiments, the determining device communication system automatically transmits the communication including the data indicative of the determined concentration of the analyte in the user to the infusion device communication system. In other particular embodiments, the characteristic determining device further includes a user input device for inputting commands, and the determining device communication system transmits the communication including the data indicative of the determined concentration of the analyte in the user to the infusion device communication system in response to a command from the user input device. In further particular embodiments, the characteristic determining device includes an indicator to indicate a status of the communication including the data indicative of the determined concentration of the analyte in the user being transmitted from the determining device communication system to the infusion device communication system.

In some embodiments, the infusion device further includes a bolus estimator used in conjunction with the infusion device processor for calculating an estimated amount of fluid to be infused into the body of the user based upon the received data indicative of the determined concentration of the analyte in the user and a target concentration of the analyte in the user. The infusion device also includes an infusion device indicator to indicate when the estimated amount of fluid to be infused has been calculated. In other embodiments, the infusion device further includes a memory for storing data, and the data indicative of the determined concentration of the analyte in the user received by the infusion device communication system from the determining device communication system is stored in the memory of the infusion device.

In additional embodiments, the determining device processor has unique identification information, and the communication transmitted from the determining device communication system to the infusion device communication system further includes the unique identification information of the determining device processor such that the infusion device is capable of discerning whether the communication is intended for receipt by the infusion device. In yet additional embodiments, the infusion device processor has unique identification information, and the communication transmitted from the determining device communication system to the infusion device communication system further includes the unique identification information of the infusion device processor such that the infusion device is capable of discerning whether the communication is intended for receipt by the infusion device.

In further embodiments, the determining device communication system is capable of being deactivated and reactivated. The characteristic determining device may also include a memory for storing data indicative of the determined concentration of the analyte in the user that is determined when the determining device communication system is deactivated. The determining device communication system then transmits a communication including the stored data to the infusion device communication system when the determining device communication system is reactivated.

In still further embodiments, the infusion device processor uses power cycling whereby power is periodically supplied to the infusion device communication system until a communication is received from the determining device communication system. The infusion device processor discontinues using power cycling whereby the power is continuously supplied to the infusion device communication system when the communication including the data indicative of the determined concentration of the analyte in the user is received from the determining device communication system. Further, the infusion device processor resumes using power cycling upon completing the receipt of the communication including the data indicative of the determined concentration of the analyte in the user from the determining device communication system.

In other embodiments, the infusion system further includes a connector for coupling the characteristic determining device to a computer and downloading data from the characteristic determining device to the computer. The infusion device communication system is further capable of transmitting a communication including infusion device data to be downloaded, and the determining device communication system is further capable of receiving the communication including the infusion device data to be downloaded from the infusion device communication system. The received infusion device data is then downloaded from the characteristic determining device through the connector to the computer.

In yet other embodiments, the characteristic determining device further includes a determining device clock, and the infusion device further includes an infusion device clock. The infusion device communication system further transmits a communication including a time of the infusion device clock, and the determining device communication system further receives the communication including the time of the infusion device clock from the infusion device communication system. The determining device clock is then set to the received time of the infusion device clock. Alternatively, the determining device communication system further transmits a communication including a time of the determining device clock, and the infusion device communication system further receives the communication including the time of the determining device clock from the determining device communication system. The infusion device clock is then set to the received time of the determining device clock.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
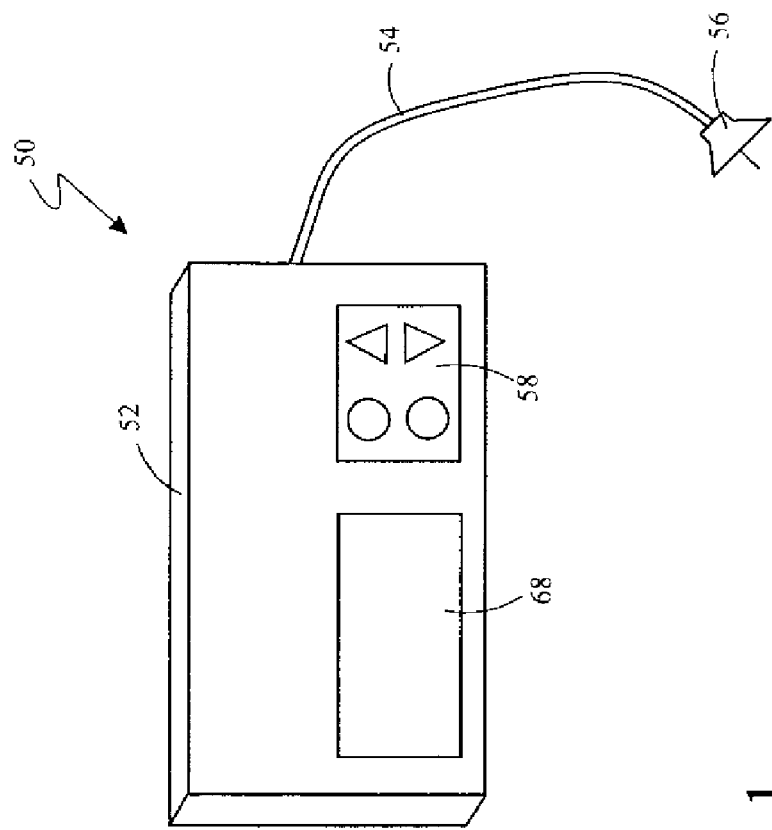
FIG. 1 is a perspective view of a blood glucose meter and an infusion pump in accordance with an embodiment of the present invention.
Figure 1:
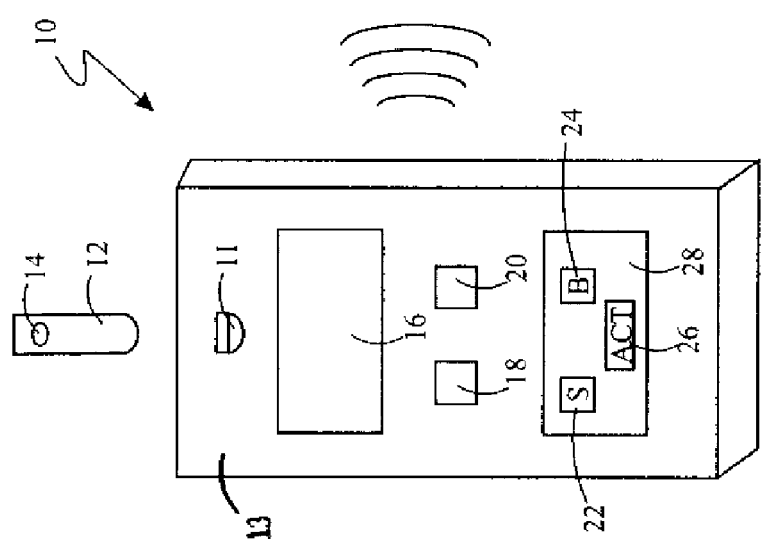

As shown in the drawings for purposes of illustration, the invention is embodied in a system for communicating blood glucose measurements from a blood glucose measurement device to an electronic computing device, which utilizes the blood glucose measurements to calculate a bolus estimate. In preferred embodiments, the blood glucose (BG) measurement device is a blood glucose (BG) test strip meter, and the electronic computing device is an insulin delivery device, preferably an external insulin infusion pump. The BG meter utilizes a test strip with a sample of the user's blood to measure the user's BG level, and then transmits the BG measurement to the infusion pump using a communication system that includes, for example, a radio frequency (RF) transmitter or transceiver. The infusion pump receives the BG measurement from the BG meter, and includes bolus estimation software to calculate a bolus estimate using the received BG measurement. The infusion pump may then deliver a bolus amount to the user based on the calculated bolus estimate. Transmission of the BG measurement from the BG meter to the infusion pump eliminates user transcription errors (i.e., the user may not accurately enter the BG measurement into the infusion pump) and simplifies the use of a bolus estimator. In particular embodiments, the BG meter may also function as a remote controller for the infusion pump, so the user can initiate a bolus delivery (without the bolus estimator) or stop a bolus delivery using buttons located on the BG meter. The BG meter may further function as a communications link for downloading data from the infusion pump to a computer or the like.

However, in alternative embodiments of the present invention, the BG measurement device may be a continuous glucose measurement system, a hospital hemacue, an automated intermittent blood glucose measurement system, and the like, and/or the BG measurement device may use other methods for measuring the user's BG level, such as a sensor in contact with a body fluid, an optical sensor, an enzymatic sensor, a fluorescent sensor, a blood sample placed in a receptacle, or the like. In further alternative embodiments, the electronic computing device may be another type of insulin delivery device, such as an implantable insulin infusion pump or system that uses a combination of implantable and external components, an injection pen, an IV meter, and the like. In other alternative embodiments, the electronic computing device may be a computer, the Internet, a personal digital assistant (PDA), a portable telephone, a custom computing device, and the like. In still further alternative embodiments, the BG measurement device may use samples from body fluids other than blood, such as interstitial fluid, spinal fluid, saliva, urine, tears, sweat, or the like. In yet other alternative embodiments, other measurement devices may be utilized to determine the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like. In still other alternative embodiments, other fluids may be delivered to the user, such as medication other than insulin (e.g., HIV drugs, drugs to treat pulmonary hypertension, iron chelation drugs, pain medications, and anti-cancer treatments), chemicals, enzymes, antigens, hormones, vitamins, or the like. Particular embodiments are directed towards the use in humans; however, in alternative embodiments, the infusion devices may be used in animals.

In preferred embodiments of the present invention, a blood glucose (BG) measurement device measures a user's BG level and then communicates the BG measurement to an electronic computing device, which utilizes the BG measurement to calculate a bolus estimate. In the embodiment illustrated in FIG. 1, the BG measurement device is a BG test strip meter 10, and the electronic computing device is an insulin delivery device, preferably an external insulin infusion pump 50.

Figure 4A:
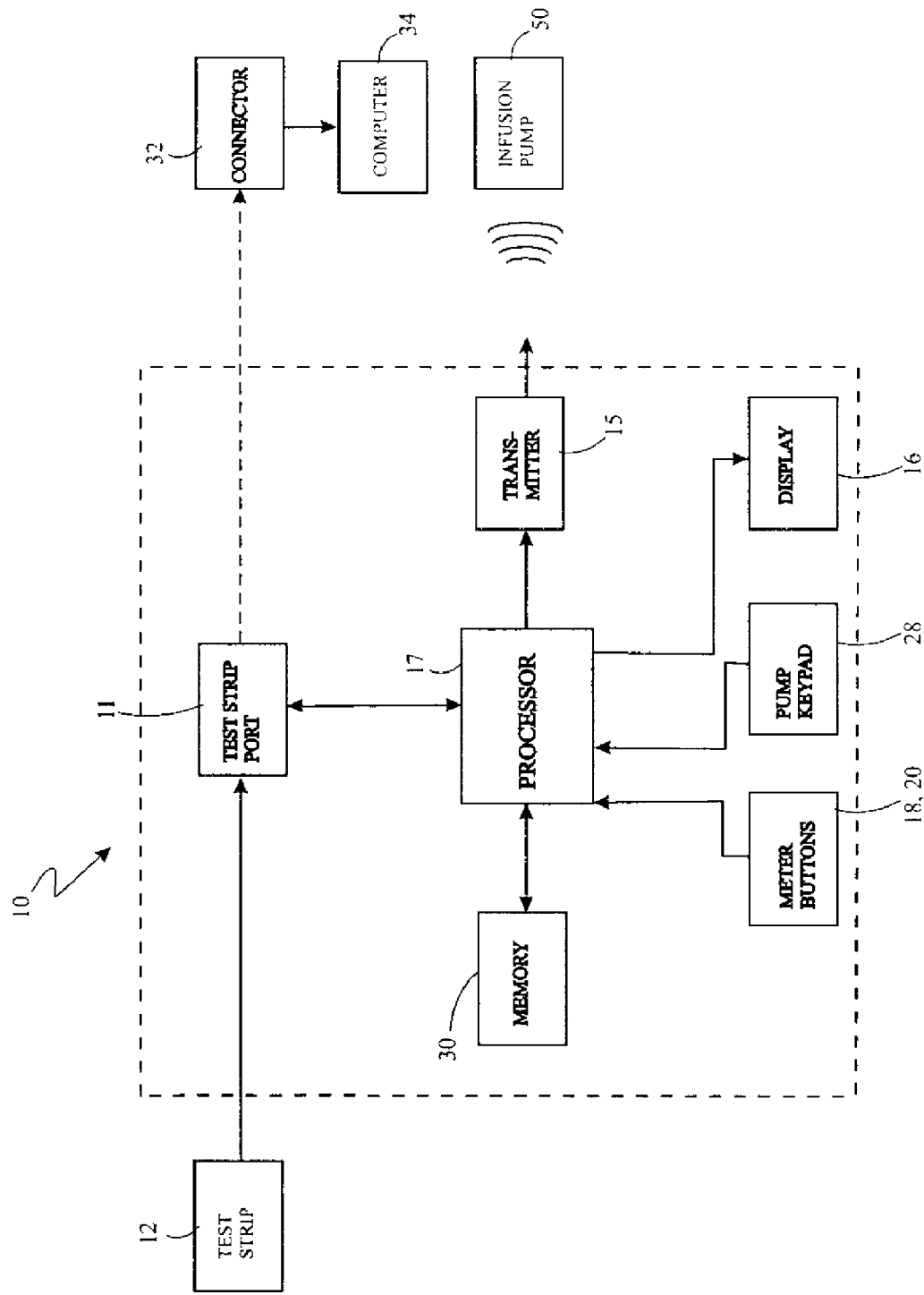
FIG. 4(a) is a simplified block diagram of a blood glucose meter in accordance with an embodiment of the present invention.

Referring to FIGS. 1 and 4(a), a housing 13 of the BG meter 10 preferably includes a test strip receptacle or port 11 for receiving and analyzing a test strip 12 or the like with a sample of the user's blood 14 on the test strip 12 to obtain a BG measurement. The BG meter 10 is adapted to be carried by the user, for example, in the hand, on the body, in a clothing pocket, attached to clothing (e.g., using a clip, strap, adhesive, or fastener), and the like. In particular embodiments, the user may utilize a separate lancing device (not shown) to obtain a blood sample, and then apply the sample onto the test strip 12. In other particular embodiments, the BG meter 10 may incorporate a lancing device (not shown) that obtains and automatically applies the blood sample onto the test strip 12.

In alternative embodiments, the BG measurement device may be a continuous glucose measurement system, a hospital hemacue, an automated intermittent blood glucose measurement system, and the like, and/or the BG measurement device may use other methods for measuring the user's BG level, such as a sensor in contact with a body fluid, an optical sensor, an enzymatic sensor, a fluorescent sensor, a blood sample placed in a receptacle, or the like. The BG measurement device may generally be of the type and/or include features disclosed in U.S. patent application Ser. No. 09/377,472 filed Aug. 19, 1999 and entitled "Telemetered Characteristic Monitor System and Method of Using the Same," Ser. No. 09/334,996 filed Jun. 17, 1999 and entitled "Characteristic Monitor with a Characteristic Meter and Method of Using the Same," Ser. No. 09/487,423 filed Jan. 20, 2000 and entitled "Handheld Personal Data Assistant (PDA) with a Medical Device and Method of Using the Same," and Ser. No. 09/935,827 filed Aug. 23, 2001 and entitled "Handheld Personal Data Assistant (PDA) with a Medical Device and Method of Using the Same," which are herein incorporated by reference. Such BG measurement devices may be adapted to be carried by the user, for example, in the hand, on the body, in a clothing pocket, attached to clothing (e.g., using a clip, strap, adhesive, or fastener), and the like. In further alternative embodiments, the BG measurement device may use samples from body fluids other than blood, such as interstitial fluid, spinal fluid, saliva, urine, tears, sweat, or the like. In yet other alternative embodiments, other characteristic determining or measuring devices may be utilized to determine or measure the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like.

In particular embodiments, once the BG meter 10 obtains a BG measurement, the BG measurement is transmitted to the infusion pump 50 using a communication system, which includes a radio frequency (RF) transmitter 15, as will be described below. In other particular embodiments, the RF transmitter 15 may be replaced with an RF transceiver 19 (as shown in FIG. 4(b)) or 36 (as shown in FIG. 5), and the BG measurement may be transmitted to the infusion pump 50 using the RF transceiver 19 or 36.

The test strip port 11 and RF transmitter 15 are coupled to a processor 17 contained in the housing 13 of the BG meter 10. The processor 17 runs programs and controls the BG meter 10, and is also connected to a memory 30 for storing programs, history data, user defined information and parameters, and the like. The BG meter 10 also preferably includes a display 16 for providing the BG measurement and/or messages, such as status or error messages, to the user. In particular embodiments, the display 16 may include a backlight for reading the display 16 in the dark.

Figure 4B:
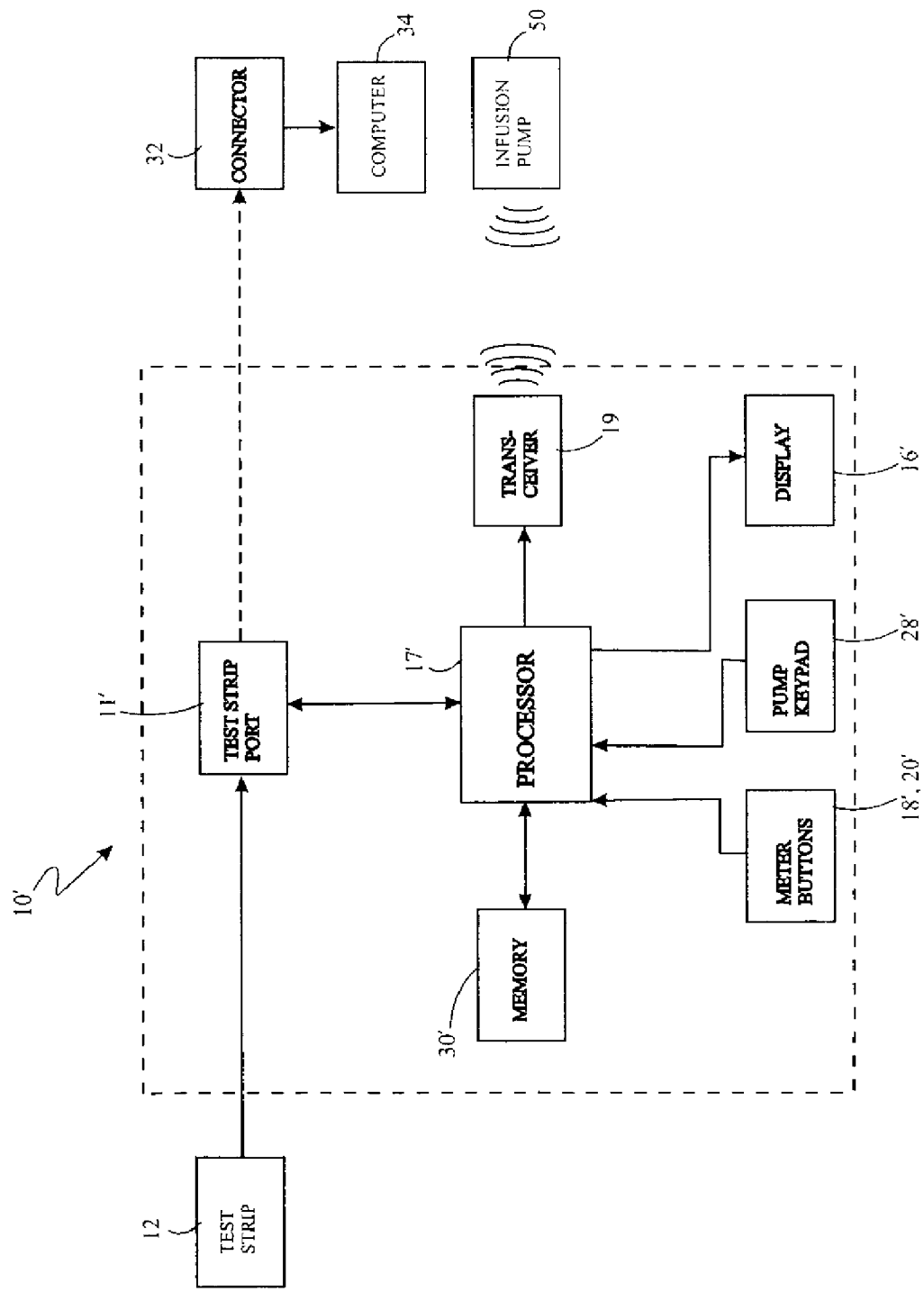
FIG. 4(b) is a simplified block diagram of a blood glucose meter in accordance with another embodiment of the present invention.
Figure 5:
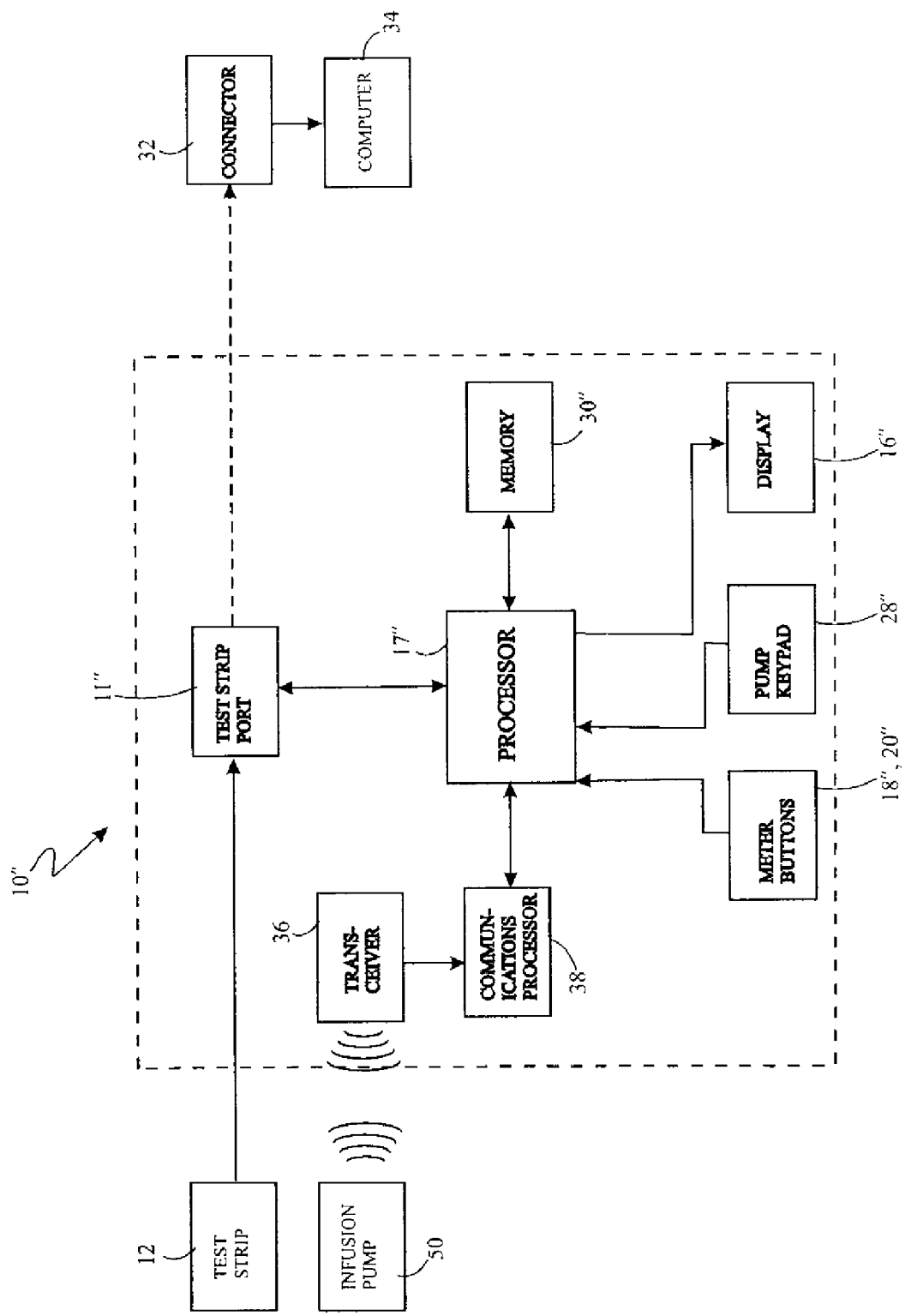
FIG. 5 is a simplified block diagram of a blood glucose meter in accordance with still another embodiment of the present invention.

In preferred embodiments, the BG meter 10 includes one or more buttons 18 and 20 for operation of the meter 10, such as turning on/off the meter 10, reviewing previous BG measurements, transmitting BG measurements to the infusion pump 50, turning off the transmitter 15 (or transceiver 19 (shown in FIG. 4(b)) or 36 (shown in FIG. 5)) in the BG meter 10 so that it does not send a BG measurement to the infusion pump 50, and the like. The BG meter 10 may further include a keypad 28 with one or more buttons 22, 24, and 26 that are preferably dedicated to remotely controlling the infusion pump 50, for example, via the RF transmitter 15 (or RF transceiver 19 (as shown in FIG. 4(b)) or 36 (as shown in FIG. 5)), as will be described below. The buttons 22, 24, and 26 may also be used to transmit BG measurements to the infusion pump 50. The buttons 22, 24, and 26 may be labeled 'S' for "suspend", 'B' for "bolus", and 'ACT' for "activate". In alternative embodiments, more or less buttons for operating the meter 10 and/or remotely controlling the infusion pump 50 may be included on the meter 10, and the buttons may be labeled other than as illustrated in FIG. 1. For example, the BG meter 10 may include an additional button for operating a lancing device (not shown) that is incorporated into the meter 10. In further alternative embodiments, the buttons 22, 24, and 26 may be omitted, and the buttons 18 and 20 may be used to remotely control the infusion pump 50. In other alternative embodiments, the buttons 18 and 20 may be omitted, and the buttons 22, 24, and 26 may be used to operate the BG meter 10, or alternatively, no buttons may be needed to operate the meter 10. For example, the meter 10 may include no buttons or other user interface or input device, and may be controlled using an external device, such as a remote programmer (not shown), the infusion pump 50, a PDA, or the like. In yet other alternative embodiments, one or more of the buttons 18, 20, 22, 24, and 26 may be omitted, and the user may utilize other input devices to interface with the BG meter 10, such as selecting a menu item, utilizing the display 16 as a touch screen, pressing multi-function keys, or the like.

In addition to transmitting the BG measurement to the infusion pump 50, the BG meter 10 also preferably stores the BG measurement in the memory 30 of the BG meter 10 for subsequent analysis and review. A history of alarms or error messages generated by the BG meter 10, as well as remote control commands sent to and/or information received from the infusion pump 50, may also be stored in the memory 30 of the BG meter 10. Further, the user may periodically cause the BG meter 10 to download the stored data through an interface (such as the RF transmitter 15 (or RF transceiver 19 (as shown in FIG. 4(b)) or 36 (as shown in FIG. 5)), a cable, a communication station, or the like), to a computer 34, or alternatively, over the Internet to a remote server for storage. In particular embodiments, a connector 32 may be inserted into the test strip port 11 to provide a wired connection to a USB, serial, or the like port of the computer 34, and data may be downloaded from the BG meter 10 through the connector 32 to the computer 34. The user or a caregiver (e.g., the user's parent, health care professional, educator) can evaluate the user's therapy by accessing the historical BG measurements and insulin delivery information downloaded from the pump 50, as will be described below.

Figure 2:
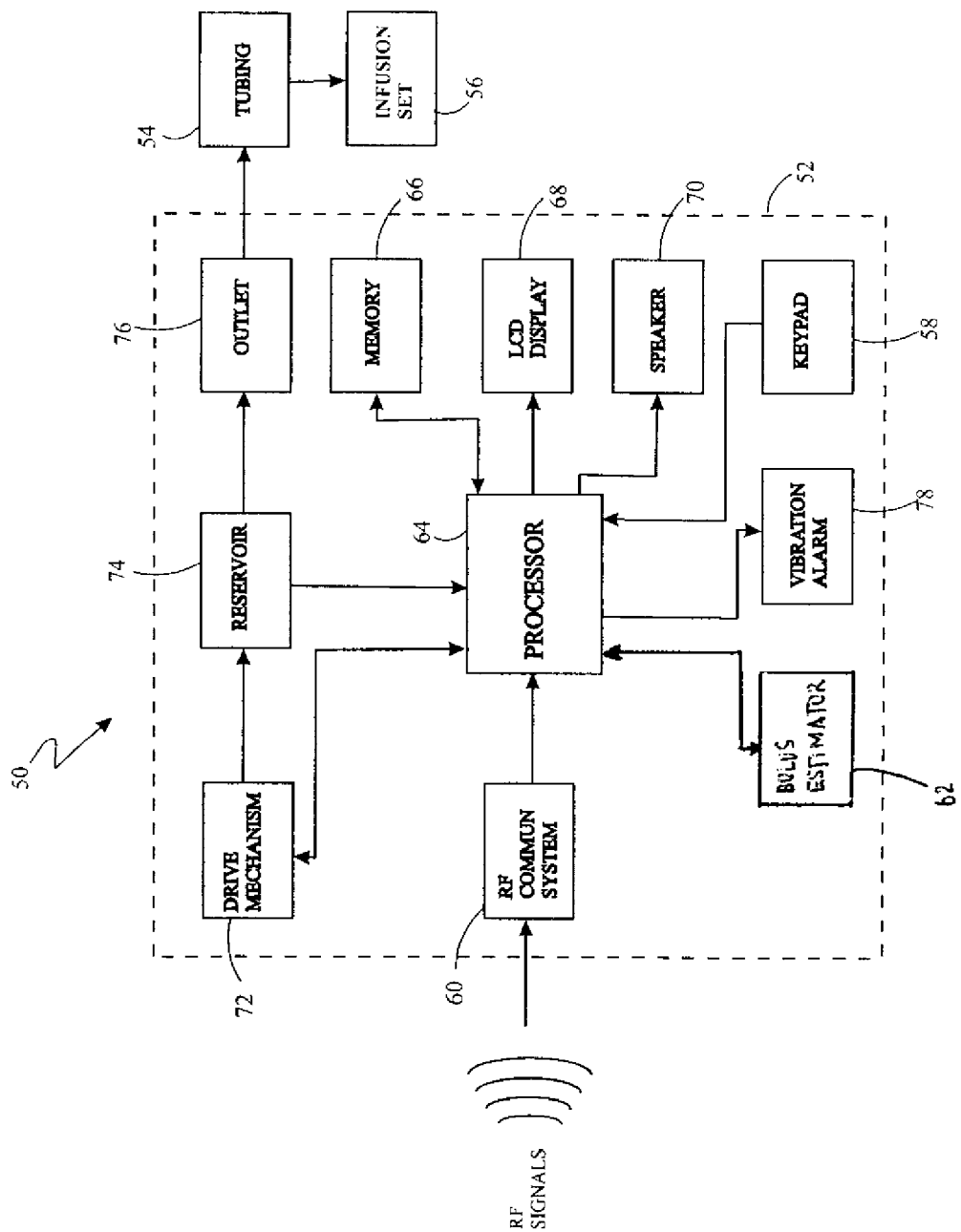
FIG. 2 is a simplified block diagram of an infusion pump in accordance with an embodiment of the present invention.

In the embodiment illustrated in FIGS. 1 and 2, the electronic computing device is an insulin delivery device, preferably an external insulin infusion pump 50. The infusion pump 50 regulates the flow of fluid from the infusion pump 50, through a flexible tube 54, and into an infusion set 56 or the like that is adhered to the individual. Infusion sets 56 that may be used as a delivery device are described in, but not limited to, U.S. Pat. Nos. 4,723,947; 4,755,173; 5,176,662; 5,584,813; and 6,056,718, which are herein incorporated by reference. The infusion pump 50 may be of the type described in U.S. Pat. Nos. 4,562,751; 4,685,903; 5,080,653; 5,097,122; 5,505,709; and 6,248,093; and disclosed in U.S. patent application Ser. No. 09/334,858, filed Jun. 17, 1999 and entitled "Infusion Pump With Remote Programming and Carbohydrate Calculator Capabilities," which are herein incorporated by reference. Such infusion pumps 50 may be adapted to be carried by the user, for example, in the hand, on the body, in a clothing pocket, attached to clothing (e.g., using a clip, strap, adhesive, or fastener), and the like. Alternatively, other infusion pumps 50 may be used for delivery of fluid through an infusion set 56 into an individual's body. In further alternative embodiments, devices other than infusion pumps 50 may be used for delivery of fluid into an individual's body, such as an implantable insulin infusion pump or system that uses a combination of implantable and external components, an injection pen, an IV meter, and the like. In other alternative embodiments, the electronic computing device may be a computer, the Internet, a personal digital assistant (PDA), a portable telephone, a custom computing device, and the like.

Figure 3A:
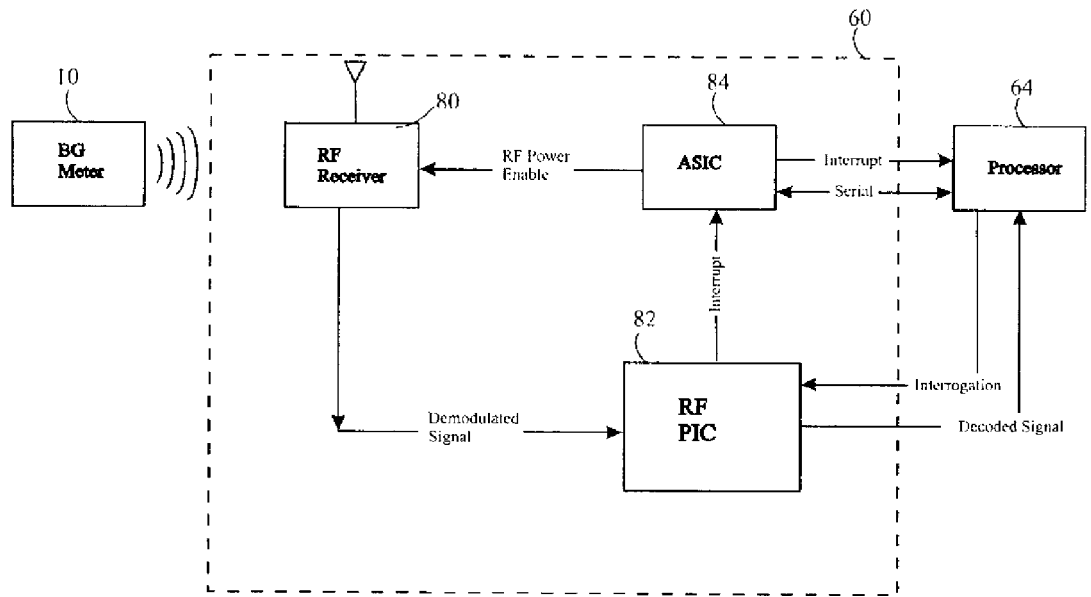
FIG. 3(a) is a block diagram of an RF communication system in the infusion pump in accordance with an embodiment of the present invention.
Figure 3B:
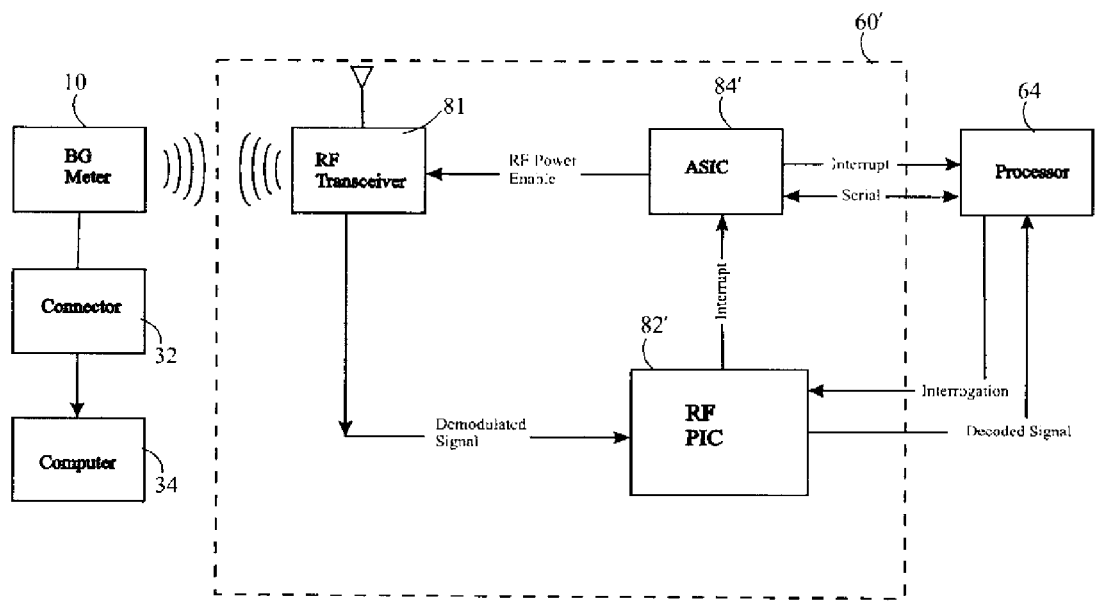
FIG. 3(b) is a block diagram of an RF communication system in the infusion pump in accordance with another embodiment of the present invention.

As illustrated in FIGS. 1 and 2, preferred embodiments of the infusion pump 50 include an RF communication system 60 and a bolus estimator 62. In particular embodiments, the RF communication system 60 includes an RF receiver 80, as shown in FIG. 3(a), which allows one-way communication from the BG meter 10 (or other external devices such as a remote programmer for the infusion pump 50) to the infusion pump 50. In other particular embodiments, the RF communication system 60' may include an RF transceiver 81, as shown in FIG. 3(b), which allows two-way communication between the BG meter 10 (or other external devices such as a remote programmer for the infusion pump 50) and the infusion pump 50.

The RF communication system 60 and bolus estimator 62 communicate with a processor 64 contained in a housing 52 of the infusion pump 50. The processor 64 is used to run programs and control the infusion pump 50, and is connected to an internal memory device 66 that stores programs, history data, user defined information and parameters. In preferred embodiments, the memory device 66 is a ROM and DRAM; however, in alternative embodiments, the memory device 66 may include other memory storage devices, such as RAM, EPROM, dynamic storage such as flash memory, energy efficient hard-drive, or the like. In the illustrated embodiment, the processor 64 is also coupled to a drive mechanism 72 that is connected to a fluid reservoir 74 containing fluid, which is delivered through an outlet 76 in the reservoir 74 and housing 52, and then into the user's body through the tubing 54 and the infusion set 56.

The infusion pump 50 is preferably programmed through a user input device such as a keypad 58 on the housing 52, or alternatively, by commands received from an RF programmer (not shown) through the RF communication system 60. The infusion pump 50 may also be programmed through the keypad 58 on the BG meter 10, for example, through the RF communication system 60, as will be described below. Feedback to the infusion pump 50 on status or programming changes are shown on a display 68, audibly through a speaker 70, and/or tactilely through a vibration alarm 78. The infusion pump 50 may also provide the user with an alarm either audibly via the speaker 70 and/or tactilely via the vibration alarm 78, such as a warning that is indicative of a low reservoir situation or low battery. Alarms may start out at a low level and escalate until acknowledged by the user. In alternative embodiments, the keypad 58 may include more or less keys or different key arrangements than those illustrated in FIG. 1. In further alternative embodiments, the keypad 58 may be omitted, and the display 68 may be used as a touch screen input device. In other alternative embodiments, the keypad 58, display 68, speaker 70, and/or vibration alarm 78 may be omitted, and all programming and data transfer may be handled through the RF communication system 60.

In particular embodiments, one-way communication is provided from the BG meter 10 to the infusion pump 50. The BG meter 10 includes the RF transmitter 15 (shown in FIG. 4(a)), and the infusion pump 50 includes an RF receiver 80 (shown in FIG. 3(a)). In other particular embodiments, two-way communication is provided between the BG meter 10 and the infusion pump 50. The RF transmitter 15 in the BG meter 10 is replaced with an RF transceiver 19 (shown in FIG.

4(b)) or 36 (shown in FIG. 5), and the RF receiver 80 in the infusion pump 50 is replaced with an RF transceiver 81 (shown in FIG. 3(b)).

The infusion pump 50 may provide several programming options, including the bolus estimator 62, as well as remote and on-device programming. The infusion pump 50 may also be configured through an interface, such as a cable or communication station, using a computer or the like. Additionally, the infusion pump 50 may allow the user to download information in the memory 66 through the interface to a computer or the like, or alternatively, over the Internet to a remote server, for storage. Further description of a communication station of this general type may be found in U.S. Pat. No. 5,376,070, which is herein incorporated by reference. The user or a caregiver (e.g., the user's parent, health care professional, educator) can evaluate the user's therapy by accessing the historical BG measurements downloaded from the BG meter 10 and insulin delivery information downloaded from the pump 50.

Information may also be downloaded from the infusion pump 50 through the RF communication system 60. Referring to FIG. 3(b), the RF communication system 60' may include the RF transceiver 81 for transmitting information to and receiving information from external devices. In particular embodiments, an external communication link (not shown) may be connected to a serial, USB, or the like port of a computer. Information may be transmitted from the RF transceiver 81 in the infusion pump 50 to an RF transceiver in the external communication link (not shown), which then downloads the information through a wired connection to the computer or the like. During the download process, the communication link may draw power from the computer through the serial, USB, or the like port. In other particular embodiments, the connector 32 may be inserted into the test strip port of the BG meter 10' to provide a wired connection to a USB, serial, or the like port of the computer 34, as shown in FIG. 4(b). Information may be transmitted from the RF transceiver 81 in the infusion pump 50 to the RF transceiver 19 in the BG meter 10', and may then be downloaded through the connector 32 to the computer 34. The BG meter 10' merely functions as a "pass through" connection between the infusion pump 50 and the computer 34. During the download process, power may be drawn from the power supply (not shown) for the BG meter 10' (e.g., battery or the like), or alternatively, from the USB, serial, or the like port of the computer 34. In still other particular embodiments, information may be transmitted from the RF transceiver 81 in the infusion pump 50 to the RF transceiver 36 in the BG meter 10", as shown in FIG. 5. The information may be transmitted from the infusion pump 50 to the BG meter 10" at a rate higher than can be handled by the meter processor 17". Accordingly, the BG meter 10" may include a communications microcontroller or processor 38 with a higher processing speed (e.g., 10 MHz) than the meter processor 17" with a lower processing speed (e.g., 1-4 MHz). The transmitted information is first processed by the communications processor 38, then processed by the meter processor 17", and finally downloaded through the connector 32 to the computer 34. Again, the BG meter 10' merely functions as a "pass through" connection between the infusion pump 50 and the computer 34. In alternative embodiments, information may be transmitted from the infusion pump 50 and stored in the memory 30' or 30" of the BG meter 10' or 10" for subsequent downloading from the BG meter 10' or 10" to the computer 34. In further alternative embodiments, information may be transmitted from the infusion pump 50 through the BG meter to the computer 34 using other modes of communication, such as infrared, optical, or the like.

In preferred embodiments, the infusion pump 50 communicates with various external devices, such as the BG meter 10, a remote programmer, and a communication station, using the RF communication system 60, which will be described below. The infusion pump 50 also provides a confirmation to the user upon receipt of a communication from another device (e.g., the BG meter 10). In particular embodiments, the infusion pump 50 provides one or more audible signals when it has received a communication. More than one audible signal may be used, and each audible signal indicates the type of communication that was received. For example, the infusion pump 50 may beep 4 times when it has received a communication to deliver 0.4 units of insulin in a bolus, provide a long low tone when it has received a communication to suspend insulin delivery, and/or sound off with a two-tone "door bell" sound when a new BG measurement has been communicated. In alternative embodiments, the infusion pump 50 may provide other forms of confirmation when a communication has been received, such as one or more vibrations via the vibration alarm 78, messages on the display 68, lights or flashing lights, or the like.

In preferred embodiments, once the BG meter 10 obtains a BG measurement, the BG meter 10 automatically transmits the BG measurement to the infusion pump 50. In particular embodiments, the BG meter 10 analyzes the blood sample 14 on the test strip 12 to calculate a BG measurement and then transmits the BG measurement to the infusion pump 50 without additional effort by the user. In alternative embodiments, the BG measurement is transmitted when the test strip 12 is removed from the BG meter 10. In other alternative embodiments, the BG meter 10 transmits the BG measurement in response to an action by the user. The BG meter 10 may also retransmit the BG measurement to the infusion pump 50 in response to a user action, such as pressing a button, selecting a menu item, or holding down a button on the BG meter 10, aligning the BG meter 10 and the infusion pump 50, or the like. In alternative embodiments, the BG meter 10 is notified by the infusion pump 50 to transmit or retransmit the BG measurement.

Once the infusion pump 50 receives the BG measurement, the infusion pump 50 may provide an alarm or warning to the user if the received BG measurement is above or below glycemic limits. The glycemic limits are preferably programmable, such as 120 mg/dl for hyperglycemia and 60 mg/dl for hypoglycemia. The user, a caregiver, a physician, a parent, a guardian, a child, or the like may program other limits into the infusion pump 50. In alternative embodiments, the glycemic limits are not programmable. In preferred embodiments, the infusion pump 50 will suspend insulin delivery if the received BG measurement is below the hypoglycemic limit. The infusion pump 50 may also notify the user to activate a bolus delivery if the received BG measurement is above the hyperglycemic limit. In alternative embodiments, the infusion pump 50 does not compare the received BG measurement to glycemic limits, and does not suspend insulin delivery in the event of hypoglycemia or notify the user to activate bolus delivery in the event of hyperglycemia.

In preferred embodiments, the infusion pump 50 also stores the received BG measurement in its memory 66. Further, the bolus estimator 62 in the infusion pump 50 may utilize the received BG measurement to calculate a bolus estimate, either automatically or in response to user input, such as through the keypad 58, a remote programmer, or the like. Once the bolus estimate is calculated and provided to the user, for example, on the display 68, the user may then approve the recommended estimate for delivery into the body, modify the recommended estimate for delivery into the body, or reject the recommended estimate. The bolus estimator 62 may generally be of the type and/or include features disclosed in U.S. patent application Ser. No. 09/334,858 filed Jun. 16, 1999, now issued U.S. Pat. No. 6,554,798 issued Apr. 29, 2003.

The BG meter 10 preferably informs the user of the status of the BG measurement calculation and/or transmission. If the infusion pump 50 is capable of only one-way communication, such notification is preferable because no confirmation is received from the infusion pump 50 indicating that the transmitted data has been received by the pump 50. The BG meter 10 may notify the user when a blood sample is being analyzed to obtain a BG measurement. The BG meter 10 may also notify the user when the BG measurement is being transmitted to the infusion pump 50. The BG meter 10 may further notify the user when the transmission of the BG measurement is complete. Once notified that the transmission of the BG measurement is complete, the user may access the bolus estimator 62 in the infusion pump 50 to view the BG measurement and calculate a bolus. In preferred embodiments, the BG meter 10 displays the status on the display 16, for example, as an alphanumeric message, a graphical icon, or the like. In alternative embodiments, the status is communicated to the user in other ways, such as using one or more light emitting diodes, one or more audible tones, a speaker, a piezo electric device, a vibrator or other tactile device, or the like. In further alternative embodiments, the BG meter 10 may not provide the status to the user. For example, if the BG measurement device provides continuous or automatic intermittent BG measurements, the user is not perpetually notified regarding the status of the calculations and/or transmissions.

In preferred embodiments, the BG meter 10 keeps track of the elapsed time between when a BG measurement is collected and when it is communicated to the infusion pump 50 for calculating a bolus estimate. A BG measurement is preferably used to calculate a bolus estimate only if the BG measurement is recent enough. The bolus estimation is at least partially dependent on the difference between the user's present BG level and a desired target BG level. Since a user's BG level varies over time, using an old BG measurement to calculate a bolus estimation might result in a bolus estimation that is inappropriate for the user. A BG measurement is expired (and is not used for bolus estimation) when it is too old to be considered representative of the user's present BG level. The BG meter 10 does not transmit a BG measurement to the infusion pump 50 for use in a bolus estimation calculation if the BG measurement is expired. The BG meter 10 may also indicate to the user that a new BG measurement is required because the BG measurement is expired or unavailable. In preferred embodiments, the BG measurement expires at 10 minutes. In alternative embodiments, the BG measurement may expire in an amount of time greater or less than 10 minutes, such as 5 or 7 minutes, 15 or 30 minutes, 1 hour, or the like. In further alternative embodiments, the time required for a BG measurement to expire may be set by the user, a caregiver, a physician, a parent, a guardian, a child, and the like. For example, a child's BG level may change more quickly than that of a heavy adult, so the BG meter 10 may be set so that BG measurements older than 5 minutes cannot be communicated to the infusion pump 50 for use in a bolus estimation. To continue the example, an adult might program the BG meter 10 so that BG measurements expire after 12 minutes. Furthermore, the time required for a BG measurement to expire may be set depending on the time of the user's most recent bolus dose of medication. A first period may be set if the user has taken a bolus within a specified duration of time, and a second period may be set if the user has not taken a bolus within the specified duration of time. For example, the time required for a BG measurement to expire may be set to 5 minutes if the user has taken a bolus within the past 2 hours, and to 15 minutes if the user has not taken a bolus within the past 2 hours.

In preferred embodiments, the infusion pump 50 does not use an expired BG measurement in a bolus estimation calculation. The infusion pump 50 preferably keeps track of the time between when a new BG measurement is received from the BG meter 10 and when the new BG measurement is used in a bolus estimation calculation. In particular embodiments, once the BG meter 10 obtains a BG measurement, the BG measurement is immediately transmitted to the infusion pump 50, either automatically or in response to a user action. Thus, when the infusion pump 50 receives a BG measurement, the pump 50 knows that the BG measurement was recent, and can calculate the approximate age of the BG measurement simply by determining the amount of time that has elapsed between when the BG measurement was received from the BG meter 10 and when the BG measurement is used in a bolus estimation calculation. In other particular embodiments, the infusion pump 50 is told the age of the BG measurements it receives. In other words, the elapsed time between when a BG measurement is collected and when it is communicated to the infusion pump 50 is transmitted along with each BG measurement. Then, the infusion pump 50 can calculate the age of the BG measurement by adding the age of BG measurement at the time it was transmitted to the time that has passed since the BG measurement was received. Since the infusion pump 50 knows the age of the BG measurement, the infusion pump 50 can eliminate BG measurements that are expired and/or prevent expired BG measurements from being used in a bolus estimation calculation. In particular embodiments, the infusion pump 50 will request a new BG measurement from the user when the user attempts to use a bolus estimator and the BG measurement is expired or unavailable.

In alternative embodiments, an estimate of the user's BG level is used for bolus estimation. In particular alternative embodiments, the user's BG level is estimated using the last BG measurement, the age of the BG measurement, the amount of insulin that has been delivered, the insulin action time, the number of carbohydrates consumed, the carbohydrate/insulin ratio, and the like. In further alternative embodiments, the estimate of the user's BG level will expire if not used soon enough. In still further alternative embodiments, the estimate of the user's BG level may only be calculated for a certain period after a BG measurement is collected. In other alternative embodiments, the length of time that a BG estimate may be calculated since a BG measurement was collected is determined by the amount of insulin that has been delivered, the amount of carbohydrates the user has ingested, the user's insulin sensitivity, and/or by the user's insulin action time. For example, estimates of BG levels may be calculated for a longer period if the user has not eaten lately and is using only basal insulin. If the user has eaten or taken a bolus of insulin, then the period of time that an estimate of the user's BG level might be calculated is shorter.

In preferred embodiments, the BG meter 10 communicates with the infusion pump 50 using RF communication. In alternative embodiments, other modes of communication may be used, such as infrared (IR), wired, ultrasonic, sonic, optical, and the like. The BG meter 10 transmits one or more BG measurements to the infusion pump 50. The BG meter 10 may also communicate one or more remote control commands to the infusion pump 50. The available commands preferably include a bolus amount of insulin, a command to begin insulin delivery, and a command to suspend insulin delivery. In alternative embodiments, more or less remote control commands may be provided between the BG meter 10 and the infusion pump 50. The RF transmitter 15 (or RF transceiver 19 (as shown in FIG. 4(*b*)) or 36 (as shown in FIG. 5)) in the BG meter 10 transmits the data (e.g., BG measurements or remote control commands) to the RF communication system 60 in the infusion pump 50. Additionally, the infusion pump 50 may communicate one or more user-defined parameters to the BG meter 10 (e.g., the time required for a BG measurement to expire). The RF transceiver 81 in the infusion pump 50 (shown in FIG. 3(*b*)) transmits such parameters to the RF transceiver 19 (as shown in FIG. 4(*b*)) or 36 (as shown in FIG. 5) in the BG meter 10' or 10".

In preferred embodiments, communication between the BG meter 10 and the infusion pump 50 contains unique identifying information about the BG meter 10 and/or infusion pump 50, such as the BG meter's 10 and/or infusion pump's 50 serial number, identification number, a password, a code, or the like. In particular embodiments, the unique identifying information about the BG meter 10 and/or infusion pump 50 included in the communication between the BG meter 10 and the infusion pump 50 is used by the respective devices (i.e., BG meter 10 and/or infusion pump 50) to discern between communications that are intended for the device and those that are not. In alternative embodiments, other codes may be included in communications between the BG meter 10 and the infusion pump 50 that are used by the respective devices to recognize which communications are intended for the device, such as an identification code for the device, a password, a bit sequence, a special frequency, timing between communications, or the like.

In preferred embodiments, the communication system in the BG meter 10 may be deactivated, preferably by the user. When the communication system is deactivated, the BG meter 10 will not attempt to communicate with other devices, including the infusion pump 50. For example, when a new BG measurement is available, the BG meter 10 will not communicate the BG measurement to another device, such as the infusion pump 50. In particular embodiments, the BG meter 10 includes an RF transmitter 15 (shown in FIG. 4(*a*)) (or RF transceiver 19 (shown in FIG. 4(*b*)) or 36 (shown in FIG. 5)) that can be deactivated and reactivated by the user. This is especially useful if the BG meter 10 transmits at frequencies that might disrupt an airplane during take-off. In alternative embodiments, other devices may be used to deactivate and reactivate the communication system in the BG meter 10, such as the infusion pump 50, other insulin delivery device, a computer, PDA, portable telephone, or the like. In preferred embodiments, the BG meter 10 may be programmed to reactivate its communication system after a certain duration. In particular embodiments, when the user deactivates the BG meter's communication system, the user is prompted to enter a duration for how long communication system is to be deactivated, and the communication system will automatically become active at the end of the duration. In alternative embodiments, the user may specify a time of day for the communication system to become active. In particular embodiments, all of the BG measurements that have been generated while the communication system was deactivated are transmitted to the infusion pump 50 when the communication system is reactivated. Other data may also be transmitted to the infusion pump 50, such as the BG meter's clock time when the BG measurement was generated (i.e., the timestamp for the BG measurement), the age of the BG measurement, and the like.

One-way communication is preferably used between the BG meter 10 and the infusion pump 50. The BG meter 10 includes a transmitter 15, and the infusion pump 50 includes a receiver 80. For example, the BG meter 10 transmits data (e.g., BG measurements or remote control commands), and the infusion pump 50 receives this data. The benefits of one-way communication (compared to two-way) include cheaper unit costs, less development time, and decreased battery power requirements. However, the drawback of one-way communication is that there is no confirmation that the BG meter 10 has transmitted the data to the infusion pump 50. Accordingly, in alternative embodiments, two-way communication may be used, and the BG meter 10 may include a transceiver 19 (as shown in FIG. 4(*b*)) or 36 (as shown in FIG. 5), and the infusion pump 50 may include a transceiver 81 (as shown in FIG. 3(*b*)).

In preferred embodiments, the infusion pump 50 uses power cycling to periodically supply power to its communication system. In alternative embodiments, the infusion pump 50 may not use power cycling, and instead, may continuously supply power to its communication system. The power cycle, which is one period that the communication system is off plus one period that the communication system is on, is preferably 8 seconds. In alternative embodiments, the power cycle may be shorter or longer than 8 seconds, such as 2 or 4 seconds, 12 or 15 seconds, or the like. Further, the period that the communication system is on during each power cycle is preferably 48 milliseconds (ms). In alternative embodiments, the period that the communication system is on during each power cycle may be greater or less than 48 ms, depending on the length of the message to be received, the communication frequency, the speed of the communication system electronics, and the like. In preferred embodiments, the BG meter 10 sends repeated signals to the infusion pump 50 for a period longer than the power cycle. The signal sent from the BG meter 10 to the infusion pump 50 preferably includes a command that is short enough to be captured during the on-time of the infusion pump's communication system. In particular embodiments, the command is short enough to be captured multiple times (i.e., two, three, or more times) during the on-time of the infusion pump's communication system.

In preferred embodiments, the time that the infusion pump's communication system must be on to capture the command from the BG meter 10 is short compared to the power cycle. In further embodiments, the command is short compared to a string of information. When the infusion pump 50 receives a command, the infusion pump 50 stops power cycling the communication system and turns the communication system on continuously. Alternatively, when the infusion pump 50 receives a command, the infusion pump 50 may continue to use power cycling unless the command indicates that the pump 50 should prepare to receive a string of information. Thus, short commands may be used to activate the infusion pump's communication system so that one or more longer strings of information may be received by the infusion pump 50.

In particular embodiments, the infusion pump 50 prepares to receive a string of information longer than a command. The string of information preferably includes a BG measurement. The string of information may further include an elapsed time since the BG measurement was taken. In alternative embodiments, the string of information may include a clock time. In further alternative embodiments, the BG meter 10 may transmit a clock time to the infusion pump 50 so that the infusion pump 50 can determine the difference between the BG meter's clock and the infusion pump's clock. In other alternative embodiments, the infusion pump 50 may use the BG meter's clock time to reset the infusion pump's clock time.

In preferred embodiments, the infusion pump 50 returns to power cycling the communication system after information has been received from the BG meter 10. In particular embodiments, the infusion pump 50 returns to power cycling after it receives a complete signal containing a BG measurement from the BG meter 10. In alternative embodiments, the infusion pump 50 returns to power cycling at a predetermined period after a signal from the BG meter 10 has stopped. In other alternative embodiments, the infusion pump 50 returns to power cycling at a predetermined period after receiving a signal from the BG meter 10.

As described above, the infusion pump 50 preferably communicates with various external devices, such as the BG meter 10, using the RF communication system 60. In particular embodiments, the RF communication system 60 includes an RF receiver 80, an RF microcontroller 82 (RF PIC), and an application specific integrated circuit 84 (ASIC), as shown in FIG. 3(a). In other particular embodiments, the RF receiver 80 may be replaced with an RF transceiver 81, as shown in FIG. 3(b). The RF PIC 82 may hold a 7-byte word, although in alternative embodiments, the RF PIC 82 may hold other lengths of data. The processor 64 communicates with the RF PIC 82 and the ASIC 84 using synchronous peripheral interfaces (SPI interfaces).

The RF receiver 80 receives and demodulates RF signals, extracts a data packet from the RF signal, and passes the data packet to the RF PIC 82. The RF PIC 82 accepts and decodes the data packet and checks for format. If the format of the data packet is valid, the RF PIC 82 sends an interrupt signal to the ASIC 84. When the ASIC 84 receives an interrupt signal from the RF PIC 82, the ASIC 84 sends an interrupt to the processor 64, triggering the processor 64 to notify the RF PIC 82 to pass the contents of its buffer to the processor 64. The processor 64 acquires the decoded data packet from the RF PIC 82 and evaluates the content, which may include a command or information to be stored. In response to some data packets, the processor 64 will send a command to the ASIC 84 to change the power conditions on the RF receiver 80. The processor 64 also processes the commands and information received from the BG meter 10, which may result in changing the bolus delivery on the infusion pump 50 or entering a BG measurement into the bolus estimator 62. One of the main tasks for the ASIC 84 is to enable and disable power on the RF receiver 80. Generally, the ASIC 84 cycles the power on the RF receiver 80 to save energy. If commanded by the processor 64, however, the ASIC 84 will enable the RF receiver 80 to be powered continuously.

Each RF transmission sent to the pump preferably includes an RF signal header followed by a command packet or an information packet. Since the pump's RF receiver 80 is likely to wake up in the middle of a command packet, the RF signal header at the start of each transmission helps the pump 50 to synchronize its data sampling and identify the first byte of a new command packet or information packet. The RF signal header is preferably the same for each transmission, and is transmitted at the start of each RF transmission. The RF signal header may include two parts: a preamble and a start signature. The preamble is a series of pulses used to train the pump's digital signal sampling, and allows the pump 50 to synchronize its pulse sampling with the pulse bits in the new transmission. The start signature notifies the pump RF PIC 82 when the first byte of a new packet is starting. In alternative embodiments, the RF signal header may include other data. In further alternative embodiments, the RF signal header may be omitted.

In particular embodiments, command packets are 7 bytes in length, and information packets are 71 bytes in length. In alternative embodiments, the command packets and/or information packets may be of different lengths. The last byte of every command or information packet is an 8-bit cyclic redundancy check (CRC) calculated on all the preceding bytes in the packet. Before a command or information packet is sent by the BG meter 10 to the infusion pump 50, it is encoded using a DC balanced encoding scheme, which translates 4 bits of data into 6 for transmission as follows:

| HEX | DC |
|---|---|
| 0 | 010101 |
| 1 | 110001 |
| 2 | 110010 |
| 3 | 100011 |
| 4 | 110100 |
| 5 | 100101 |
| 6 | 100110 |
| 7 | 010110 |
| 8 | 011010 |
| 9 | 011001 |
| A | 101010 |
| B | 001011 |
| C | 101100 |
| D | 001101 |
| E | 001110 |
| F | 011100 |

The result of the encoding is that the 7-byte command packets require transmission of 11 bytes and the 71-byte data packets require transmission of 107 bytes. Upon receipt of the 11-byte or 107-byte packets from the BG meter 10, the pump RF PIC 82 in the infusion pump 50 decodes the packet into the 7-byte command packet or the 71-byte information packet. The processor 64 then checks all packets for valid identification of the infusion pump 50 (e.g., identification or serial number) and CRC. If the identification of the infusion pump 50 is not valid, the packet is ignored. If the CRC of the first command packet is not valid, the command is ignored. Otherwise, the processor 64 sends a negative acknowledge (NAK) response to any packet with an invalid CRC.

Information packets (71 bytes) are much larger than command packets (7 bytes), and cannot be stored in the pump RF PIC 82, and thus, cannot be used to "wake up" the pump 50. Instead, a command packet must be sent to the pump 50 to turn on the pump's RF receiver 80 and prepare the pump 50 to receive an information packet. While power to the infusion pump's communication system (i.e. RF receiver 80) is being cycled, a command packet is repeatedly transmitted from the BG meter 10 to the infusion pump 50. If an RF signal (i.e. including the first command packet) is present when the pump's RF receiver 80 comes on, the pump 50 will attempt to store the contents of the signal in the pump RF PIC 82. The processor 64 will verify whether the content of the signal is a valid command packet. If the command packet is valid, then the pump 50 will stop power cycling and power the RF receiver 80 continuously. Only the first command packet must be transmitted repeatedly. After the RF receiver 80 is on full-time, other command packets can be sent to the pump 50 in quick succession (for example, as quickly as the user can press buttons on the BG meter 10 or other external device to send the new command packets). Additional command packets or an information packet may also be transmitted to the pump 50.

The pump 50 preferably recognizes two categories of command packets: remote control or bolus commands and BG measurement commands. Remote control or bolus commands directly control the pump's insulin bolus delivery. BG measurement commands may transmit a new BG measurement(s) from the BG meter 10 to the pump 50, or alternatively, prepare the pump 50 to receive an information packet containing a new BG measurement value as well as other related data (e.g., a clock time or timestamp of the BG measurement, the age of the BG measurement, or the like) from the BG meter 10.

The pump 50 may receive a bolus command from the BG meter 10 or a remote programmer associated with the pump 50. The bolus command preferably includes a type code indicating the type of device transmitting the message (e.g., the BG meter 10 or the remote programmer), unique identifying information about the pump 50 (e.g., serial number, identification number, password, or the like), a key code indicating which bolus command button has been pressed (e.g., button "S" 22, button "B" 24, or button "ACT" 26 on the BG meter 10), and a counter indicating the number of times that the button has been pressed. In alternative embodiments, the bolus command may include other information and/or omit some of this data. When the pump 50 receives the bolus command, the processor 64 filters the command to discern the counter value so that the pump 50 can respond to the number of times the user has pressed the button to adjust a bolus.

The pump 50 may also receive a BG measurement command from the BG meter 10. The BG measurement command is transmitted to the pump 50 to send a new BG measurement(s) from the BG meter 10 to the pump 50, or alternatively, to prepare the pump 50 to receive an information packet containing a new BG measurement as well as other related data (e.g., a clock time or timestamp of the BG measurement, the age of the BG measurement, or the like) from the BG meter 10. If the BG measurement command transmits a new BG measurement(s) from the BG meter 10 to the infusion pump 50, the command preferably includes a type code indicating the type of device transmitting the message (e.g., the BG meter 10), the BG measurement value(s), and unique identifying information about the meter 10 and/or pump 50 (e.g., serial number, identification number, password, or the like). If the BG measurement command is transmitted to prepare the pump 50 to receive an information packet containing a BG measurement and other related data from the BG meter 10, the command preferably includes a type code indicating the type of device transmitting the message (e.g., the BG meter 10), unique identifying information about the meter 10 and/or pump 50 (e.g., serial number, identification number, password, or the like), and a key code indicating that a new BG measurement is about to be transmitted. In alternative embodiments, the BG measurement command may include other information and/or omit some of this data.

In response to communications from the BG meter 10, the pump 50 typically sends an acknowledge (ACK) response. However, in particular embodiments, the BG meter 10 does not include an RF receiver, and the pump 50 does not include an RF transmitter, and thus, the pump 50 does not send an ACK response if the type code in the command (e.g., bolus or BG measurement command) indicates that the device transmitting the message is the BG meter 10. In alternative embodiments, both the BG meter 10 and the pump 50 may include an RF transmitter and receiver (i.e. transceiver 19 (shown in FIG. 4(b)) or 36 (shown in FIG. 5) in the BG meter 10' or 10", and transceiver 81 (shown in FIG. 3(b)) in the infusion pump 50), and thus, the pump 50 may send an ACK response to the BG meter 10. Additionally, the pump 50 may send its clock time to the BG meter 10, and the BG meter 10 may use the pump's clock time to reset the BG meter's clock time if the devices' clock times do not correspond with one another. Further, if the meter 10 does not receive an ACK response from the pump 50, the meter 10 may attempt to retransmit the communication to the pump 50, either immediately or at a later time.

When the pump 50 receives a command packet from the BG meter 10, the processor 64 will send a data packet through the ASIC 84, commanding the RF receiver 80 to remain on full-time for a specified number of minutes, to receive other command packets or an information packet. The RF receiver 80 may return to power cycling after the information packet has been received, a certain period of time after receiving a BG measurement command (in the event that the anticipated information packet does not arrive), a certain period of time after receiving a bolus command, or after the battery in the pump 50 has been removed and replaced.

The pump RF PIC 82 remains in receive mode unless it has received a command to send from the processor 64, in which case it shall switch to transmit mode until the transmission is complete. Once the data has been transmitted, the pump RF PIC 82 automatically switches back to receive mode.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion system for infusing a fluid into a body of a user, the infusion system comprising:
    a characteristic meter device including:
        a meter device housing to be carried by the user;
        a test strip receptacle coupled to the meter device housing for receiving and testing an analyte from the user to determine a concentration of the analyte in the user;
        a meter device processor contained in the meter device housing and coupled to the receptacle for processing the determined concentration of the analyte from the receptacle;
        a meter device indicator to indicate the determined concentration of the analyte in the user; and
        a meter device communication system contained in the meter device housing and coupled to the meter device processor for automatically transmitting a communication including data indicative of the determined concentration of the analyte in the user, wherein the meter device indicator further indicates when the communication including the data indicative of the determined concentration of the analyte in the user is being transmitted from the meter device communication system; and
    an infusion device including:
        an infusion device housing to be carried by the user;
        a drive mechanism contained in the infusion device housing and operatively coupled with a reservoir containing the fluid for infusing the fluid into the body of the user;
        an infusion device communication system contained in the infusion device housing for receiving the communication including the data indicative of the determined concentration of the analyte in the user from the meter device communication system;
        an infusion device processor contained in the infusion device housing and coupled to the infusion device communication system for processing the data indicative of the determined concentration of the analyte in the user and controlling the infusion device;

an infusion device indicator to indicate the determined concentration of the analyte in the user when the communication including the data indicative of the determined concentration of the analyte in the user has been received by the infusion device communication system from the meter device communication system; and a bolus estimator used in conjunction with the infusion device processor for calculating an estimated amount of fluid to be infused into the body of the user based upon the received data indicative of the determined concentration of the analyte in the user and a target concentration of the analyte in the user, wherein the infusion device processor determines an amount of time that has elapsed since the data indicative of the determined concentration of the analyte in the user was received from the meter device communication system, and prevents the bolus estimator from calculating the estimated amount of fluid to be infused based upon the determined concentration of the analyte if the elapsed amount of time exceeds a predetermined amount of time, and causes the bolus estimator to calculate the estimated amount of fluid to be infused based upon the determined concentration of the analyte if the elapsed amount of time does not exceed the predetermined amount of time, and wherein the infusion device indicator further indicates when the estimated amount of fluid to be infused has been calculated.

2. The infusion system according to claim 1, wherein the infusion device processor uses power cycling such that power is periodically supplied to the infusion device communication system until a communication is received from the meter device communication system, and further wherein the infusion device processor discontinues using power cycling such that the power is continuously supplied to the infusion device communication system when the communication including the data indicative of the determined concentration of the analyte in the user is received from the meter device communication system.

3. The infusion system according to claim 2, wherein the infusion device processor resumes using power cycling upon completing receipt of the communication including the data indicative of the determined concentration of the analyte in the user from the meter device communication system.

4. The infusion system according to claim 1, wherein the meter device indicator further indicates when the communication including the data indicative of the determined concentration of the analyte in the user has been received by the infusion device communication system from the meter device communication system.

5. The infusion system according to claim 1, wherein the meter device processor has unique identification information, and the infusion device further comprises:

a user input device for inputting the unique identification information of the meter device processor into the infusion device; and a memory for storing the unique identification information of the meter device processor, further wherein the communication transmitted from the meter device communication system to the infusion device communication system further includes the unique identification information of the meter device processor such that the infusion device discerns whether the communication is intended for receipt by the infusion device.

6. The infusion system according to claim 1, wherein the infusion device processor has unique identification information, and the meter device further comprises:

a user input device for inputting the unique identification information of the infusion device processor into the meter device; and a memory for storing the unique identification information of the infusion device processor, further wherein the communication transmitted from the meter device communication system to the infusion device communication system further includes the unique identification information of the infusion device processor such that the infusion device discerns whether the communication is intended for receipt by the infusion device.

7. The infusion system according to claim 1, wherein the infusion device indicator further indicates that new data indicative of the concentration of the analyte in the user is required for the bolus estimator if the elapsed amount of time exceeds the predetermined amount of time.

8. The infusion system according to claim 1, wherein the infusion device processor uses power cycling such that power is periodically supplied to the infusion device communication system until a communication is received from the meter device communication system, and further wherein the infusion device processor discontinues using power cycling such that the power is continuously supplied to the infusion device communication system when a communication is received from the meter device communication system.

9. The infusion system according to claim 1, wherein the infusion device indicator further indicates when the determined concentration of the analyte in the user is above or below a predetermined level of the analyte in the user.

10. The infusion system according to claim 1, wherein the meter device communication system and the infusion device communication system communicate using one of radio frequencies and infrared frequencies.

11. The infusion system according to claim 1, wherein the meter device is a blood glucose test strip meter, and the infusion device is an insulin infusion pump.

12. The infusion system according to claim 1, wherein the meter device communication system includes one of a transmitter and a transceiver, and the infusion device communication system includes one of a receiver and a transceiver.

13. The infusion system according to claim 1, wherein the meter device further includes a meter device clock, and the infusion device further includes an infusion device clock, and wherein the infusion device communication system further transmits a communication including a time of the infusion device clock, and the meter device communication system further receives the communication including the time of the infusion device clock from the infusion device communication system, and further wherein the meter device clock is set to the received time of the infusion device clock.

14. The infusion system according to claim 1, wherein the meter device further includes a meter device clock, and the infusion device further includes an infusion device clock, and wherein the meter device communication system further transmits a communication including a time of the meter device clock, and the infusion device communication system further receives the communication including the time of the meter device clock from the meter device communication system, and further wherein the infusion device clock is set to the received time of the meter device clock.

* * * * *